(12) United States Patent
Kirshenbaum et al.

(10) Patent No.: US 8,524,663 B2
(45) Date of Patent: Sep. 3, 2013

(54) METHOD FOR SITE-SPECIFIC POLYVALENT DISPLAY ON POLYMERS

(75) Inventors: Kent Kirshenbaum, New York, NY (US); Justin M. Holub, New York, NY (US)

(73) Assignee: New York University, New York, NY (US)

(*) Notice: Subject to any disclaimer, the term of this patent is extended or adjusted under 35 U.S.C. 154(b) by 1920 days.

(21) Appl. No.: 11/714,066

(22) Filed: Mar. 5, 2007

(65) Prior Publication Data

US 2012/0122779 A1    May 17, 2012

Related U.S. Application Data

(60) Provisional application No. 60/778,864, filed on Mar. 3, 2006.

(51) Int. Cl.
*A61K 38/02* (2006.01)
*A61P 5/00* (2006.01)
*C07K 2/00* (2006.01)
*C07K 1/00* (2006.01)

(52) U.S. Cl.
USPC ............................ 514/9.7; 530/333; 530/300

(58) Field of Classification Search
None
See application file for complete search history.

(56) References Cited

U.S. PATENT DOCUMENTS

| | | | |
|---|---|---|---|
| 5,994,309 A * | 11/1999 | Mazar et al. | 514/13.3 |
| 6,153,596 A * | 11/2000 | Liotta et al. | 514/44 A |
| 6,723,858 B2 | 4/2004 | D'Amato et al. | |
| 6,869,969 B2 | 3/2005 | Huebner et al. | |
| 6,911,456 B2 | 6/2005 | MacLean et al. | |
| 2004/0161798 A1 * | 8/2004 | Kodadek | 435/7.1 |
| 2007/0232529 A1 * | 10/2007 | Mickle et al. | 514/11 |
| 2008/0227213 A1 | 9/2008 | Disney | |

FOREIGN PATENT DOCUMENTS

WO    0019994    4/2000

OTHER PUBLICATIONS

Aucagne et al., "Chemoselective formation of successive triazole linkages in one pot: "click-click" chemistry", Organic Letters, 2006, vol. 8, No. 20, pp. 4505-4507.
Barron et al., "Bioinspired polymeric materials: in-between proteins and plastics", Current Opinion in Chemical Biology, 1999, vol. 3, pp. 681-687.
Bock et al., "CuI-catalyzed alkyne-azide "click" cycloadditions from a mechanistic and synthetic perspective", Eur J Org Chem, 2006, pp. 51-68.
Bouillon et al., "Microwave assisted "click" chemistry for the synthesis of multiple labeled-carbohydrate oligonucleotides on solid support", J Org Chem, 2006, vol. 71, pp. 4700-4702.
Dalsin et al., "Bioinspired antifouling polymers", Materials Today, 2005, pp. 38-46.

(Continued)

*Primary Examiner* — Robert A Wax
*Assistant Examiner* — William Craigo
(74) *Attorney, Agent, or Firm* — Klauber & Jackson LLC

(57) ABSTRACT

The present invention relates to novel complex peptidomimetic products comprising multiple homogeneous or heterogeneous pendant groups that are site-specifically positioned along a linear oligomer or polymer scaffold and methods of making thereof. More specifically, the invention relates to N-substituted glycine peptoid oligomers or peptoids and their use as substrates for azide-alkyne [3+2]-cycloaddition conjugation reactions and subsequent additional rounds of oligomerization and cycloaddition. The methods of the invention may also be used to generate peptoid-peptide hybrid or peptide products comprising multiple homogeneous or heterogeneous pendant groups, which are positioned precisely along the linear oligomer or polymer scaffold.

21 Claims, 14 Drawing Sheets

(56) References Cited

OTHER PUBLICATIONS

Harrington et al., "Estrogen dendrimer conjugates that preferentially activate extranuclear, non-genomic versus genomic pathways of estrogen action", Molecular Endocrinology, 2006, vol. 20, No. 3, pp. 491-502.

Haynes et al., "Comblike, monodisperse polypeptoid drag-tags for DNA separations by end-labeled free-solution electrophoresis (ELFSE)", Bioconjugate Chem, 2005, vol. 16, pp. 929-938.

Hillard et al., "Ferrocene-mediated proton-coupled electron transfer in a series of ferrocifen-type breast-cancer drug candidates", Angew Chem Int Ed, 2006, vol. 45, pp. 285-290.

Hlavacek et al., "Steric effects on multivalent ligand-receptor binding: exclusion of ligand sites by bound cell surface receptors", Biophysical Journal, 1999, vol. 76, pp. 3031-3043.

Horn et al., "Incorporation of chemoselective functionalities into peptoids via solid-phase submonomer synthesis", Bioconjugate Chem, 2004, vol. 15, pp. 428-435.

Kumin et al., "Azidoproline containing helices: stabilization of the polyproline II structure by a functionalizable group", J Am Chem Soc, 2007, vol. 129, pp. 466-467.

Mammen et al., "Polyvalent interactions in biological systems: implications for design and use of multivalent ligands and inhibitors", Angew Chem Int Ed, 1998, vol. 37, pp. 2754-2794.

Osella et al., "FACS analysis of oxidative stress induced on tumour cells by SERMs", Inorganica Chimica Acta, 2005, vol. 358, pp. 1993-1998.

Patch et al., "Helical peptoid mimics of magainin-2 amide", J Am Chem Soc, 2003, vol. 125, pp. 12092-12093.

Patch et al., "Mimicry of bioactive peptides via non-natural, sequence-specific peptidomimetic oligomers", Current Opinion in Chemical Biology, 2002, vol. 6, pp. 872-877.

Pathak, "Azidonucleosides: synthesis, reactions, and biological properties", Chem Rev, 2002, vol. 102, pp. 1623-1667.

Rijkers et al., "A convenient synthesis of azido peptides by post-assembly diazo transfer on the solid phase applicable to large peptides", Tetrahedron Letters, 2002, vol. 43, pp. 3657-3660.

Sanborn et al., "In situ crosslinking of a biomimetic peptide-PEG hydrogel via thermally triggered activation of factor XIII", Biomaterials, 2002, vol. 23, pp. 2703-2710.

Seurynck et al., "Simple, helical peptoid analogs of lung surfactant protein B", Chemistry & Biology, 2005, vol. 12, pp. 77-88.

Top et al., "Synthesis, biochemical properties and molecular modelling studies of organometallic specific estrogen receptor modulators (SERMs), the ferrocifens and hydroxyferrocifens: evidence for an antiproliferative effect of hydroxyferrocifens on both hormone-dependent and hormone-independent breast cancer cell lines", Chem Eur J, 2003, vol. 9, pp. 5223-5236.

Wu et al., "Structural and spectroscopic studies of peptoid oligomers with alpha-chiral aliphatic side chains", J Am Chem Soc, 2003, vol. 125, pp. 13525-13530.

Wu et al., "Helical peptoid mimics of lung surfactant protein C", Chemistry & Biology, 2003, vol. 10, pp. 1057-1063.

Zhang et al., "Solid phase synthesis of peptidotriazoles with multiple cycles of triazole formation", Tetrahedron Letters, 2006, vol. 47, pp. 665-669.

Dondoni et al., "C-glycoside clustering on calix[4]arene, adamantane, and benzene scaffolds through 1,2,3-triazole linkers", J Org Chem, 2006, vol. 71, pp. 7546-7557.

Kolb et al., "The growing impact of click chemistry on drug discovery", Drug Discovery, 2003, vol. 8, No. 24, pp. 1128-1137.

Tornoe et al., "Peptidotriazoles on solid phase: [1,2,3]-triazoles by regiospecific copper(I)-catalyzed 1,3-dipolar cycloadditions of terminal alkynes to azides", J Org Chem, 2002, vol. 67, pp. 3057-3064.

Wan et al., "A potentially valuable advance in the synthesis of carbohydrate-based anticancer vaccines through extended cycloaddition chemistry", J Org Chem, 2006, vol. 71, pp. 8244-8249.

Jang et al., "Click to fit: versatile polyvalent display on a peptidomimetic scaffold", Organic Letters, 2005, vol. 7, No. 10, pp. 1951-1954.

Angell et al., "Peptidomimetics via copper-catalyzed azide-alkyne cycloadditions", Chem Soc Rev, 2007, vol. 36, pp. 1674-1689.

\* cited by examiner

Reaction conditions: a) 20% piperidine in NMP, RT, 3 x 8 min. b) CF3SO2-N3, CuSO4, DCM/MeOH (9/1 v/v), RT, at least 16 h. c) TFA/DCM (1/1 v/v, RT, 1 h. d) Washing step with 0.02 M diethyldithiocarbamic acid sodium salt, 3 x 10 min.

Peptoid Oligomerization

Peptoid Modification by "Click Chemistry"

17α-ethynylestradiol   17α-propynylestradiol   17α-butynylestradiol

METHOD FOR SITE-SPECIFIC POLYVALENT DISPLAY ON POLYMERS

CROSS REFERENCE TO RELATED APPLICATION

This application claims priority under 35 USC §119(e) from U.S. Provisional Application Ser. No. 60/778,864, filed Mar. 3, 2006, which application is herein specifically incorporated by reference in its entirety.

FIELD OF THE INVENTION

The present invention relates to novel complex peptidomimetic products comprising multiple homogeneous or heterogeneous pendant groups that are site-specifically positioned along a linear oligomer scaffold and methods of making thereof. More specifically, the invention relates to N-substituted glycine peptoid oligomers or peptoids and their use as substrates for azide-alkyne [3+2]-cycloaddition conjugation reactions and subsequent additional rounds of oligomerization and cycloaddition.

BACKGROUND OF THE INVENTION

Several publications and patent documents are referenced in this application in order to more fully describe the state of the art to which this invention pertains. The disclosure of each of these publications and documents is incorporated by reference herein.

Techniques in bioconjugate chemistry have provided effective tools for endowing biomolecules with novel properties. Conjugation reactions are routinely employed to modify proteins and nucleic acids so as to incorporate fluorophores, ligands, chelates, radioisotopes, affinity tags, and numerous other groups therein (G. T. Hermanson, *Bioconjugate Techniques*, Academic Press: San Diego, Calif., 1996). When performed on solid phase support, these reactions can be used to modify synthetic oligonucleotides and polypeptides with exceptional efficiency (reviewed in Virta et al., *Tetrahedron*, 2003, 59, 5137). In many cases, solid-phase conjugation reactions can be adapted for automated protocols, allowing the development of novel combinatorial libraries and microarray applications.

Polypeptides, while capable of exhibiting an extraordinary range of bioactivities, often display poor pharmacological properties. For this reason, synthetic mimics of peptides have been the focus of vigorous development by medicinal and bioorganic chemists. A variety of oligomeric peptidomimetics have been introduced that show potential as partial mimics of natural polypeptide species in that they exhibit some of the structural and functional attributes of natural polypeptides (Patch et al., *Curr. Opin. Chem. Biol.,* 2002, 6, 872). Further elaboration of peptidomimetic structures may lead to a greater range of capabilities for this promising class of molecules.

N-substituted glycine oligomers (α-peptoids) and N-substituted β-alanine oligomers (β-peptoids) are examples of a promising class of peptidomimetics. Peptoids are oligomers based on a peptide backbone, which can be produced by an efficient, automated solid-phase synthesis that facilitates the incorporation of diverse N-pendant sidechains in a sequence-specific manner. As such, peptoids are a class of non-natural, sequence-specific polymers that represent an alternative derivative of a peptide backbone, the sequence and length of which can be precisely controlled. Structurally, peptoids differ from polypeptides in that their sidechains are pendant groups of the amide nitrogen rather than the α-carbon (Simon et al., Proc. Natl. Acad. Sci. USA, 1992, 89, 9367; Zuckermann et al., J. Am. Chem. Soc., 1992, 114, 10646). Peptoids are particularly useful for biomedical applications because these molecules are largely invulnerable to protease degradation and hence are more stable than polypeptides in vivo. Peptoids have also been shown to be more cell permeable than their peptide analogues (Kwon et al. J. Am. Chem. Soc., 2007, 129, 1508). These properties enhance bioavailability. Moreover, peptoids, which are synthetically produced by definition, can be produced essentially in the absence of impurities.

Polyvalency is a powerful method utilized by nature to enhance the binding strength of bioactive ligands. Polyvalency exerts its affect by means of the display of multiple copies of one or more chemical groups. Although these groups may possess only modest binding strengths in isolation, as part of a larger complex the binding interactions can sum to provide a very strong interaction. A variety of approaches have been developed by chemists to mimic polyvalent display on polymers or dendrimers. Typically, these products exhibit limitations resulting from the difficulty of synthesis and/or the polydispersity of the scaffold. Ideally, chemists would seek to display ligands in a precise fashion in which the spacing between one or more of the conjugated groups can be controlled. Thus, there is a need for novel methods that can be used to perform multi-site chemical conjugation onto an oligomer or polymer scaffold.

SUMMARY OF THE INVENTION

As described herein, the present inventors have developed a novel and precise method for multi-site chemical conjugation onto an oligomer or polymer scaffold. The present invention describes this method and presents guidance as to how this method can be exploited to generate molecules with therapeutic and/or diagnostic potential. Indeed, the inventors have successfully constructed linear oligomers comprising either multiple homogeneous or multiple heterogeneous pendant groups using the present method.

More specifically, the present method is directed to the generation of a series of highly functionalized oligomers (e.g., peptoids) utilizing a novel sequential Cu(I) catalyzed azide-alkyne [3+2] cycloaddition (CuCAAC) reaction which is an example of, and herein referred to as, a "click chemistry" protocol. Accordingly, the present inventors have developed an efficient method that enables the conjugation of a variety of chemical moieties at precise locations along a peptidomimetic scaffold. The sequential CuCAAC reaction method introduced herein demonstrates that 1,2,3-triazole linkages are compatible with multiple rounds of oligomer (e.g., peptoid) chain elongation on solid phase support. These techniques may prove suitable for similar sequential bioconjugation of other polymers, including polypeptides, immobilized on solid phase and may be amenable to automation. Moreover, the sequential CuCAAC reaction method described herein may be used to generate hybrid oligomers, such as, for example peptoid-peptide hybrids.

As described herein, the present inventors have utilized this approach to develop peptoids functionalized with groups appropriate for biomedical applications, including moieties suitable for elaboration as constituents of therapeutics, biosensors and molecular imaging agents. One such linear oligomer comprising homogeneous pendant groups is a peptoid which displays a plurality of identical hormone groups that target a particular hormone receptor implicated in, for example, breast or prostate cancer. Multivalent linear peptoids comprising hormone groups may be used to advantage in therapeutic and/or diagnostic applications. The method of the present invention may also be used to generate a linear oligomer comprising heterogeneous pendant groups, wherein the linear oligomer is a peptoid which displays hormone groups that target a hormone receptor implicated in, for example, breast or prostate cancer and metal complexes that convey a therapeutic and/or diagnostic functionality.

DETAILED DESCRIPTION OF THE INVENTION

Figure 1:
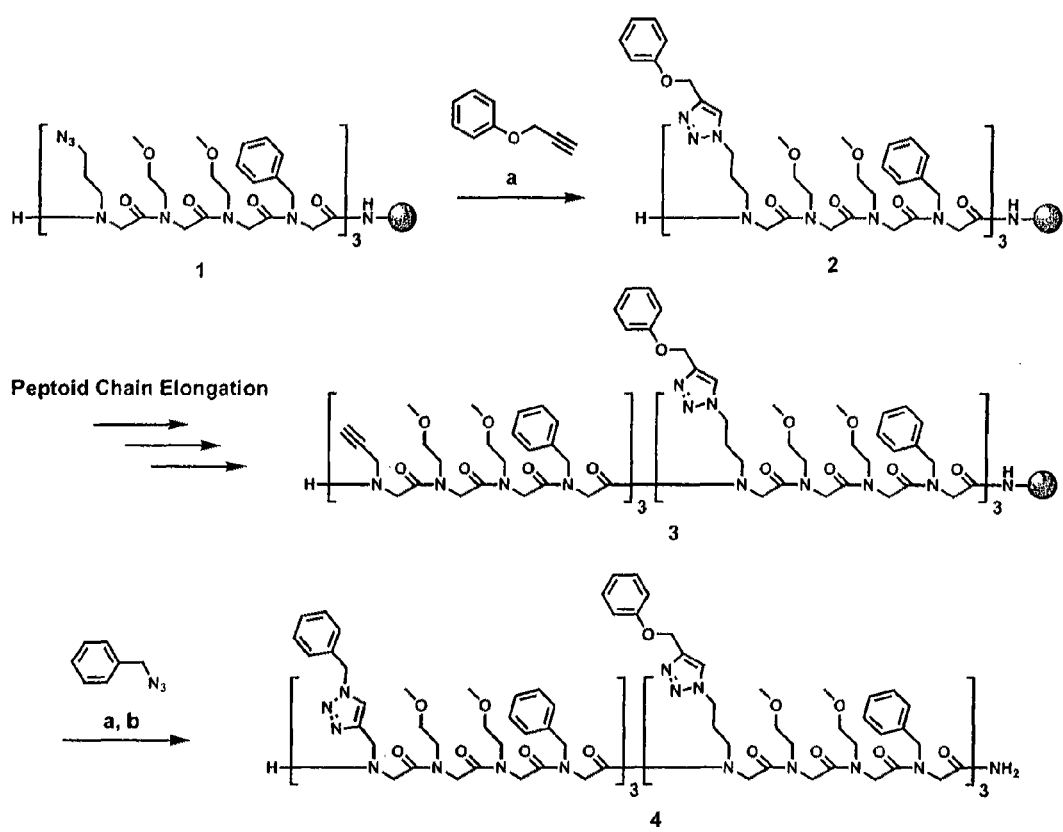
FIG. 1 (Scheme 1) depicts multi-site modification of peptoid side-chains by a sequential series of cycloaddition and oligomerization reactions. a) Coupling partner (0.06 M), CuI (0.11 M), ascorbic acid (0.06 M) and DIPEA (0.14 M) in DMF/pyridine (7/3 v/v), room temperature, 18 h. b) 95% TFA in $H_2O$, room temperature, 10 min.

The present inventors have focused on developing techniques for enhancing the structural complexity of a family of peptidomimetics known as peptoids. In a particular embodiment, these oligomers are comprised of N-substituted glycine monomer units and can exhibit a strong propensity to form stable secondary structures (Kirshenbaum et al., *Proc. Natl. Acad. Sci.* 1998, 95, 4303). Peptoids are efficiently synthesized on solid phase support to incorporate a specific sequence of chemically diverse monomer units (Zuckermann et al., *J. Am. Chem. Soc.,* 1992, 114, 10646). Advances in molecular design approaches have enabled the successful generation of peptoids that exhibit an array of biological activities (Patch et al., In *Pseudopeptides in Drug Development,* Nielsen, P. E. Ed.; Wiley-VCH: Weinheim, Germany, 2004, 1). These products may prove to be well-suited for biomedical applications due to their resistance to proteolytic degradation (Patch et al., supra). As described herein, the goal of the present inventors is to enhance the structural and functional capabilities of peptoids by developing new strategies for their chemical conjugation and ligation (Yoo et al., *J. Am. Chem. Soc.,* 2005, 127, 17132).

The CuCAAC reaction is an example of a click chemistry reaction and is gaining prominence as a versatile technique for conjugating reactants via 1,2,3-triazole formation (Kolb et al., *Drug Disc. Today,* 2003, 8, 1128). This example of a "click chemistry" reaction has been shown to be regiospecific and compatible with a wide range of substrates and reaction conditions. For example, azide-alkyne [3+2] cycloadditions have been employed to link polypeptide chains, synthesize dendrimers and conjugate derivatives to the exterior of viral particles (Franke et al., *Tetrahedron Lett.,* 2005, 46, 4479; Angelo et al., *J. Am. Chem. Soc.,* 2005, 127, 17134; Joralemon et al., *Macromolecules,* 2005, 38, 5436; Wu et al., *Chem. Comm.,* 2005, 46, 5775; Wang et al., *J. Am. Chem. Soc.,* 2003, 125, 3192; Gupta et al., *Bioconjugate Chem.,* 2005, 16, 1572). The present inventors have demonstrated the advantages of using a click chemistry approach for multi-site conjugation of alkyne- or azide-containing groups onto peptoid scaffolds (Jang et al., *Org. Lett.,* 2005, 7, 1951). Bioactive ligands typically contain chemical functionalities that are incompatible with many solid phase synthesis procedures. Due to the broad orthogonality of azide-alkyne [3+2] cycloaddition reactions, the present inventors were able to conjugate diverse ligands containing biologically relevant chemical functionalities onto peptoid scaffolds with high efficiency. The net result being a peptoid scaffold onto which a single type of biologically relevant chemical functionality is multiply conjugated (i.e., conjugated at multiple positions).

As described in detail herein below, the present inventors have developed a novel procedure to enable the sequential conjugation of multiple, diverse groups onto a single oligomer scaffold through site-specific azide-alkyne [3+2] cycloaddition methods. In order to generate peptoid substrates that allow for the consecutive addition of heterogeneous pendant groups, a procedure was devised for modifying reactive sidechain moieties and subsequently extending the oligomer scaffold. As reported herein, the technique developed utilizes a sequential series of cycloaddition and scaffold extension reactions and dramatically enhances the functionality and chemical diversity of peptoid oligomers that can be generated. The ability to perform sequential cycles of conjugation allows for the synthesis of complex modular structures in which specific functionalities are displayed in a site-directed fashion. See Examples presented herein.

As described herein, the ability to synthesize linear oligomers to which multiple, heterogeneous chemical groups are precisely attached at pre-ordained positions offers the potential to be able to generate designer molecules that are multiply polyvalent. Suitable functionalities are known to those skilled in the art and include, without limitation, hormone receptor ligands, cell surface receptor ligands, tumor specific antigen ligands, cytotoxic agents, pharmaceutical moieties, fluorophores, chelates, radioisotopes, and affinity tags.

Various constituents may be incorporated into the oligomers of the present invention to improve cellular uptake or alter subcellular localization. Poly-Arg tails, for example, are known to promote cellular uptake. Skilled practitioners would be aware of other constituents that may be included in the oligomers of the present invention to improve their uptake in cells or alter subcellular localization.

With respect to hormone receptor ligands, several modified selective hormone receptor modulators have gained prominence as potential anti-tumor agents because they selectively modulate hormone receptor activity in vitro. Current synthetic molecular design approaches for the polyvalent display of selective hormone receptor agonists typically involve dendrimer scaffolds. Chemically modified hormone ligands are covalently bound to dendrimer scaffolds that stem from a central core, resulting in polyvalent displays. While dendrimer-based agents have produced evidence of enhanced binding avidity, syntheses of these molecules usually require time-consuming and expensive multi-step chemical ligation procedures. Moreover, dendrimer syntheses generally produce a heterogeneously dispersed product that renders isolation of a pure product technically challenging, when possible. Yet another drawback associated with dendrimers is that use of dendrimer-based agents can lead to lysosomal storage disease. The present invention, therefore, offers substantial advantages with respect to both the methods involved in making dendrimers, which are time-consuming and expensive, and the dendrimeric product generated, which may contribute to disease onset. The present method, therefore, offers a far more efficient route with which to generate polyvalent molecules and produces a polyvalent linear product that is both structurally and functionally distinct from that of a dendrimer to which the same polyvalent groups have been attached.

As described herein, a polyvalent oligomer comprising a plurality of selective hormone receptor ligand conjugates may be used as an exemplary polyvalent selective hormone receptor agent. These molecules incorporate multiple hormone receptor ligands onto a single peptidomimetic scaffold. As such, these molecules are linear oligomers comprising homogeneous pendant groups, wherein the linear oligomer comprises monomers and multiple homogeneous pendant groups are attached directly to the backbone of the linear oligomer. For the synthesis of these agents, N-substituted glycine oligomer (β peptoid) scaffolds that include multiple reactive sites are generated through solid phase synthesis protocols. 17α-ethynylestradiol is ligated to the oligomer scaffold through highly regiospecific Cu catalyzed azide-alkyne [3+2] cycloaddition reactions resulting in 1,2,3 triazole linkages between the scaffold and the 17α-ethynylestradiol moieties. This rapid and efficient procedure can be used to generate peptidomimetic scaffolds that comprise polyvalently displayed hormone receptor ligands. See Examples IV and VI.

With respect to metallocenes, these are organo-metallic species in which a metal atom is sandwiched between two aromatic ligands. An exemplary metallocene is ferrocene, in which an iron atom is bound between two cyclopentadiene groups. Metallocenes in general, and ferrocenes in particular, are of interest for pharmaceutical and biosensor applications due to their redox activity. Ferrocenes, for example, can exhibit a potent cytotoxic effect primarily due to oxidative damage they cause to DNA.

Metallocene derivatives of selective hormone receptor agonists are currently being developed and their antiproliferative effects are being tested in a number of cancer cell lines. Although these agents are designed to include hormone agonists and cytotoxic agents within the same molecule, binding strengths can be low due to the monovalent display of the receptor ligand. The present invention addresses this deficiency of the available molecules by achieving polyvalent display of hormone receptor ligands and cytotoxic agents on a single scaffold.

Figure 6:
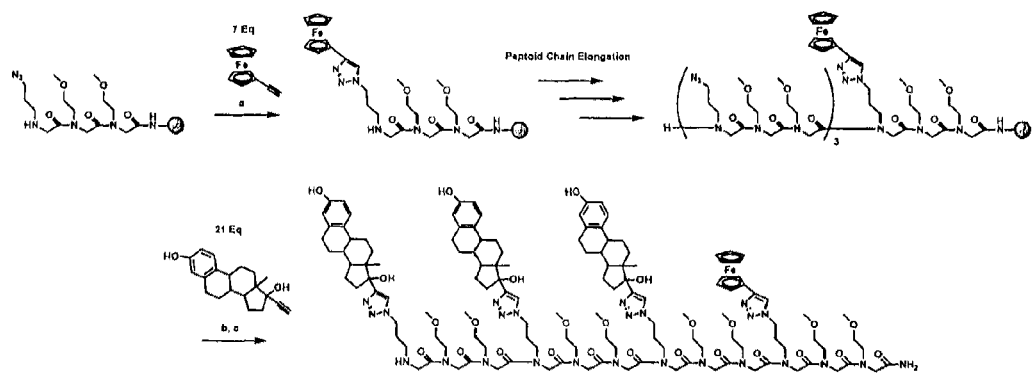
FIG. 6 (Scheme 3) depicts a general method for synthesis of polyvalent selective hormone receptor cytotoxic agents. a) CuI (0.04 M), ascorbic acid (0.02 M) and DIPEA (0.04 M) in 2-butanol/DMF/pyridine (5/3/2 v/v/v), rt, 18 h. b) CuI (0.11 M), ascorbic acid (0.06 M) and DIPEA (0.14 M) in DMF/pyridine (7/3 v/v), room temperature, 18 h. c) 95% TFA in $H_2O$, room temperature, 10 min.
Figure 7:
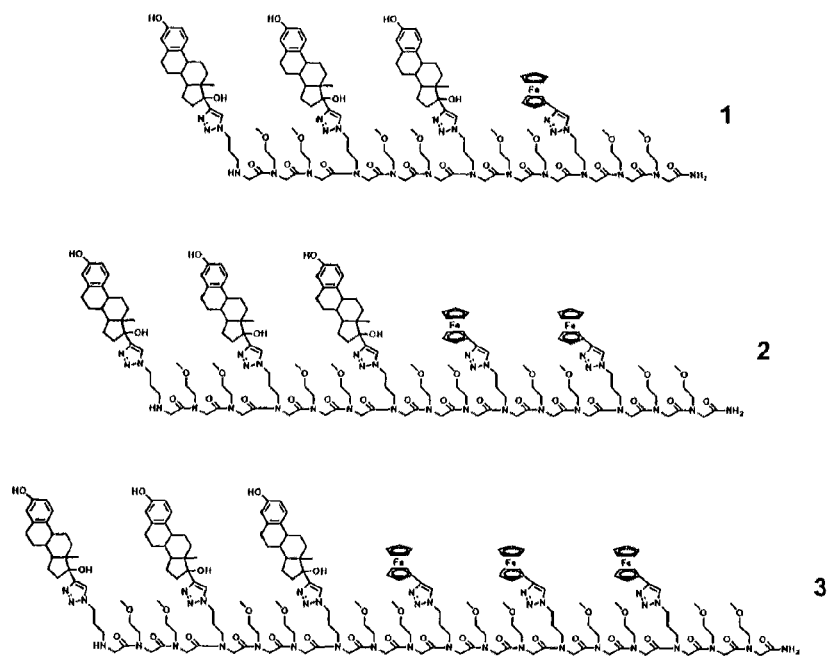
FIG. 7 shows exemplary polyvalent selective hormone receptor cytotoxic agents. Bioactive ligands are displayed on a peptidomimetic scaffold via triazole linkages. Compounds 1-3 show polyvalent display of 17α-estradiol but are not limited to that specific hormone receptor agonist. Cytotoxic metallocenes are shown in mono-, bi- and trivalent displays.

As described herein, a polyvalent oligomer comprising at least one selective hormone receptor ligand conjugate and at least one metallocene conjugate may be used as an exemplary polyvalent selective hormone receptor cytotoxic agent. These molecules are designed to incorporate multiple hormone receptor ligands and cytotoxic moieties onto a single peptidomimetic scaffold. For the synthesis of these agents, N-substituted glycine oligomer (peptoid) scaffolds including multiple reactive sites are generated through solid phase synthesis protocols. Cytotoxic metallocenes (e.g., ethynylferrocene) are ligated to the oligomer scaffold through highly regiospecific azide-alkyne [3+2] cycloaddition reactions resulting in 1,2,3 triazole linkages between the scaffold and the ethynylferrocene moieties. The oligomer chain length is then extended to include additional azide functionalities. 17α-ethynylestradiol is then ligated to the oligomer scaffold resulting in polyvalent display of the hormone receptor agonist (FIG. 6; Scheme 3). This rapid and efficient procedure can be used to generate peptidomimetic scaffolds that comprise polyvalently displayed hormone receptor ligands and cytotoxic agents (FIG. 7, Compounds 1-3).

In addition, polyvalent displays can be constructed by conjugation to macromolecular peptoid scaffolds. The term macromolecular oligomer scaffold refers to peptoids of very long chain length, up to and potentially in excess of 1,000 submonomers, which may be generated using previously described ligation procedures (Yoo et al. *J. Am. Chem. Soc.* 2005, 127, 17132). These scaffolds can be synthesized by the protease-mediated ligation of individual peptoid oligomers. The products will allow polyvalent display of from tens to hundreds of copies of the conjugated species.

It is noteworthy that conjugating bioactive ligands to peptidomimetic scaffolds via Cu(I) catalyzed azide alkyne [3+2] cycloaddition (click chemistry) demonstrates several advantages over incorporating the moieties directly as submonomers. The click chemistry method facilitates direct conjugation of commercially available azide or alkyne containing bioactive ligands to the peptoid scaffolds of the present invention without the need for further chemical modification. Additionally, many bioactive ligands contain chemical functionalities that are incompatible with many solid phase synthesis procedures. By exploiting the click chemistry method to conjugate functionalities onto a peptidomimetic scaffold, the present inventors have been able to polyvalently display diverse, bioactive ligands that would otherwise be extremely difficult or impossible to incorporate using the submonomer method.

Figure 17:
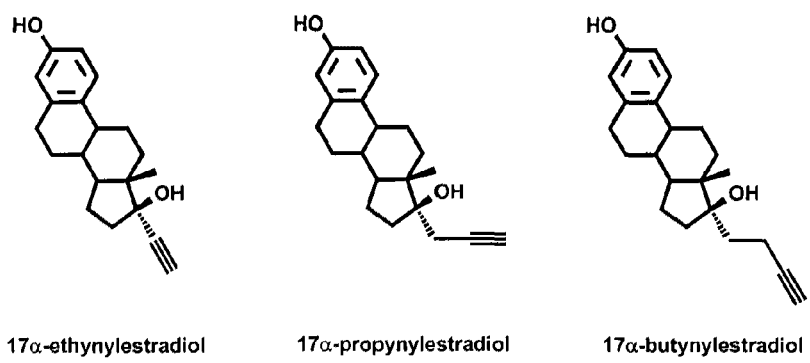
FIG. 17 depicts chemical structures of several estradiol conjugates showing extended alkyl linkers for enhanced receptor binding.

Moreover, the versatility of the present method is underscored by the ability to conjugate bioactive ligands to peptidomimetic scaffolds through linkers that separate the moieties from the scaffold backbone. When binding to receptor molecules or enzymes, bioactive ligands typically become fully sequestered within the active site of the proteins. Inclusion of a spacer (i.e., a linker) between the ligand and the scaffold may enhance the overall therapeutic effect of molecules produced using the present method by allowing the bioactive moieties to be fully incorporated into the active site. Thus, the click chemistry method conveys the freedom to control the spacing between the scaffold and the bioactive ligand, thereby limiting issues relating to steric hindrance between the bioactive ligand and the scaffold and/or other conjugated moieties. As demonstrated herein, the present inventors have been able to extend the linker between the triazole linkage and the ligand itself (See FIG. 17), with the intent that such spacing may enhance binding properties. Incorporating the moieties directly as submonomers limits this ability.

While the present inventors have shown that the click chemistry procedure described herein can be used to conjugate multiple bioactive ligands to peptoid scaffolds with high efficiency, improvements in the basic procedure are offered herein to overcome certain limitations that may arise in the context of some bioactive pendant groups. Using the basic procedure, it is necessary to wait until the last round of click chemistry to conjugate bioactive pendant groups that contain chemical functionalities that are incompatible with peptoid extension methods, such as, for example, 17α-ethynylestradiol. By modifying the sequential click chemistry method to include a step directed to protecting the incompatible chemical functionalities, greater flexibility as to the positioning of pendant group attachment sites in the oligomer sequence can be achieved.

As described herein, the method of the present invention may be used to generate cyclic oligomers comprising homogeneous or heterogeneous pendant groups. In accordance with the present method, cyclic peptoids, for example, may be generated by synthesizing a linear peptoid, cleaving it from solid phase, cyclizing the linear peptoid, and conjugating it to pendant groups at multiple sites. Cyclic oligomers may also be generated by synthesizing linear oligomers comprising homogeneous or heterogeneous pendant groups which are subsequently circularized. Cyclic oligomers (e.g., cyclic peptoids) may be used to particular advantage in the context of engaging cell surface receptor clusters. For a review detailing the use of cyclic oligomers as ligands for multivalent receptors, see Kiessling et al., *Angew Chem Int Ed Engl.*, 2006, 45, 2348, which is incorporated herein by reference in its entirety.

A skilled practitioner would appreciate that the method of the present invention may be performed in either solid phase or solution phase, or combinations thereof, depending on the desired outcome of the synthesis protocol.

The following is a non-limiting list of protecting groups that may be used in the context of the present invention. Alcohol protecting groups include, for example, Acetyl (Ac), which can be removed by acid or base; Tetrahydropyranyl ether (THP), which can be removed by acid; Methoxymethyl ether (MOM), which can be removed by acid; β-Methoxyethoxymethyl ether (MEM), which can be removed by acid; p-Methoxybenzyl ether (PMB), which can be removed by acid or hydrogenolysis; and Methylthiomethyl ether, which can be removed by acid. Amine protecting groups include, for example, Carbobenzyloxy group (CBZ), which can be removed by hydrogenolysis; Tert-butyloxycarbonyl (BOC) group, which can be removed by concentrated, strong acid (such as HCl or $CF_3COOH$); 9-Fluorenylmethyloxycarbonyl group (FMOC), which can be removed by base; and Benzyl (Bn), which can be removed by hydrogenolysis. Carbonyl protecting groups include, for example, Acetals, which can be removed by acid. Carboxylic acid protecting groups include, for example, Methyl esters, which can be removed by acid or base; and Benzyl esters, which can be removed by hydrogenolysis. A skilled practitioner would be aware of additional protecting groups of utility with respect to different pendant groups and would be able to select an alternative protecting group or groups based on his/her experience and the desired polyvalent peptoid comprising heterogeneous pendant groups to be generated.

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The terms "peptoid" and "polypeptoid" encompass both α- and β-peptoids. The following terms may be used interchangeably herein with α-peptoids, "poly (N-substituted glycines)", "oligo (N-substituted) glycines", and "oligomeric N-substituted glycines". "Peptoids" and "polypeptoids" may be produced using the methodology of the present invention. As indicated herein, peptoids are not peptides in that they are not composed of naturally-occurring amino acids linked by peptide bonds. Peptoids may, however, be designed to possess features (e.g., reactive sites) that structurally mimic naturally occurring peptides and proteins, and as such are useful as potential therapeutic agents and/or as detection reagents. The term "α-peptoid" refers to a plurality of oligomeric N-substituted glycines of any length. The term "β-peptoid" refers to a plurality of oligomeric N-substituted β-alanines of any length. More specifically, a peptoid of the invention is between 2-1,000 monomers, more particularly between 2-100 or 2-25.

Peptoids can be synthesized in a sequence-specific fashion using an automated solid-phase protocol, e.g., the sub-monomer synthetic route. See, for example, Wallace et al., Adv. Amino Acid Mimetics Peptidomimetics, 1999, 2, 1-51 and references cited therein and Patch et al., In *Pseudopeptides in Drug Development*, Nielsen, ed., Wiley-VCH, Weinheim, Germany, 2004, p. 1, all of which are incorporated herein in their entirety by this reference. The synthesis of macromolecular peptoids can be achieved using the ligation protocol as described by Yoo et al. (supra) and such peptoids may comprise alternating methoxy and benzyl side chains.

As indicated above, α-peptoids (N-substituted glycines) are non-natural, sequence specific polymers composed of a poly-glycine backbone, whereas β-peptoids (N-substituted β-alanines) are non-natural, sequence specific polymers composed of a poly-alanine backbone. Peptoid molecules contain functional groups (R) positioned as substituents of the amide nitrogen. A linear peptoid oligomer is distinct from that of a branched peptoid oligomer with respect to the nature of the characteristic "R" group. Linear peptoids contain R groups that do not include peptoid oligomers themselves. In contrast, branched peptoids are peptoids that comprise at least one R group that is a peptoid oligomer. Basic structures illustrating the structural differences exhibited by different types of peptoids are presented below.

Linear peptoid:

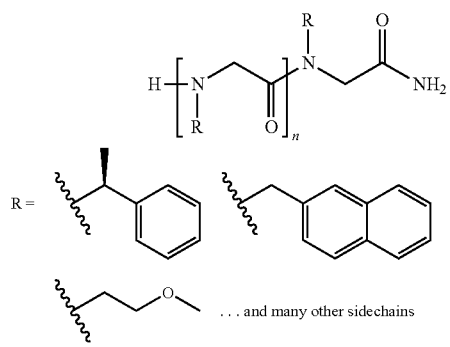

Alpha peptoid:

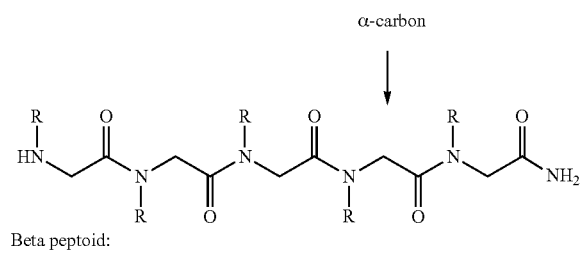

Beta peptoid:

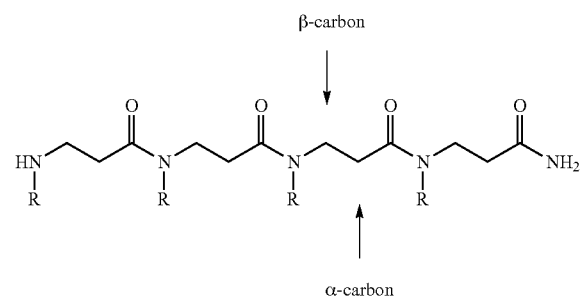

Branched peptoid:

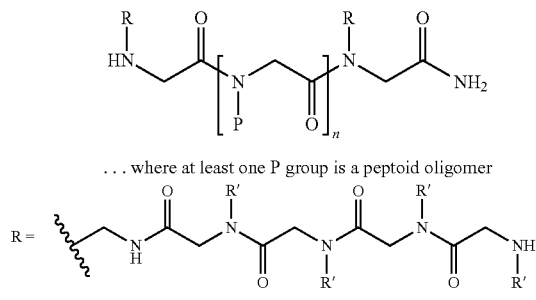

...and other peptoid oligomers of varying chain length

A "substrate" or "solid support" is a conventional solid support material used in peptide synthesis. Non-limiting examples of such substrates or supports include a variety of solid supports, including Rink Amide resin, Wang resin and Chlorotrityl resin. Connectors to the solid supports such as those which are photocleavable, DKP-forming linkers (DKP is diketopiperazine; see, e.g., WO90 09395 incorporated herein by reference), TFA cleavable, HF cleavable, fluoride ion cleavable, reductively cleavable and base-labile linkers are also encompassed herein. A solid support may also comprise a plurality of solid support particles, such as beads, which can be split into portions or "subamounts" for separate reactions and recombined as desired.

As used herein, the terms "immobilized on solid phase" or "solid support-bound" refer to molecules that are attached to a solid phase or solid support. Such attachments may be reversible in nature. A skilled practitioner is familiar with a variety of reversible attachment modes and various protocols to effect release of immobilized molecules from solid supports to which they are attached.

As described herein, the polyvalent linear and/or cyclized peptoids comprising homogeneous or heterogeneous pendant groups of the invention may be used as therapeutic and/or diagnostic molecules. Their use as potential vaccines is also encompassed herein. Polyvalent linear and/or cyclized peptoids which are glycoconjugates are also envisioned for a variety of applications. With respect to diagnostic agents, the polyvalent linear and/or cyclized peptoids comprising homogeneous or heterogeneous pendant groups of the invention may be used to advantage as molecular imaging agents, such as, without limitation, magnetic resonance imaging (MRI) contrast agents, positron emission tomography (PET) imaging agents, and optical imaging agents.

The invention also includes a composition for diagnosis or therapy comprising an effective amount of a polyvalent linear peptoid comprising homogeneous or heterogeneous pendant groups of the invention and a physiologically acceptable excipient or carrier.

Physiologically acceptable and pharmaceutically acceptable excipients and carriers for use with peptoid type reagents are well known to those of skill in the art.

By "physiologically or pharmaceutically acceptable carrier" as used herein is meant any substantially non-toxic carrier for administration in which the peptoids of the invention are stable and bioavailable when used. The peptoid can, for example, be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Water miscible carrier compositions can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

In one embodiment of the invention, the carrier comprises a sustained release or delayed release carrier. The carrier is any material capable of sustained or delayed release of the peptoid to provide a more efficient administration resulting in one or more of less frequent and/or decreased dosage of the peptoid, ease of handling, and extended or delayed effects. The carrier is capable of releasing the oligomer when exposed to the environment of the area for diagnosis or treatment or by diffusing or by release dependent on the degree of loading of the peptoid to the carrier in order to obtain peptoid release. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microphere or gel.

The compositions of the invention are administered by any suitable means, including injection, transdermal, intraocular, transmucosal, buccal, intrapulmonary, and oral. While not required, it is desirable that parenteral compositions maintain the peptoid at the desired location for about 24 to 48 hours; thus, sustained release formulations can be used, including injectable and implantable formulations.

If desired, one or more additional ingredients can be combined in the carrier: such as a moisturizer, vitamins, emulsifier, dispersing agent, wetting agent, odor-modifying agent, gelling agents, stabilizer, propellant, antimicrobial agents, sunscreen, and the like. Those of skill in the art of diagnostic pharmaceutical formulations can readily select the appropriate specific additional ingredients and amounts thereof. Suitable non-limiting examples of additional ingredients include stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulan, polymucosaccharides, hyaluronic acids, aloe vera, lecithin, polyoxyethylene sorbitan monooleate, tocopherol (Vitamin E) or the like.

More particularly, the carrier is a pH balanced buffered aqueous solution for injection. The particular carrier used, however, will vary with the mode of administration.

The compositions for administration usually contain from about 0.0001% to about 90% by weight of the peptoid compared to the total weight of the composition, more particularly from about 0.5% to about 20% by weight of the peptoid compared to the total composition, and even more particularly from about 2% to about 20% by weight of the peptoid compared to the total composition.

The effective amount of the peptoid used for therapy or diagnosis will vary depending on one or more factors such as the specific peptoid used, the age and weight of the patient, the type of formulation and carrier ingredients, frequency of use, the type of therapy or diagnosis preformed and the like. It is a matter of routine for a skilled practitioner to determine the precise amounts to use, taking into consideration these factors and the present specification.

Unless defined otherwise, all technical and scientific terms used herein have the same meaning as commonly understood by one of ordinary skill in the art to which this invention belongs. Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description, examples, and the claims.

EXAMPLE I

Methods and Materials

General:

Peptoid oligomers were characterized by analytical Reversed-Phase High Performance Liquid Chromatography (RP-HPLC) using a C4 column (Peeke Scientific, Ultra-120, 5 μm, 120 Å, 2.0×50 mm) on a Beckman Coulter System Gold HPLC system. Products were detected by UV absorbance at 214 nm with a System Gold 166 detector. Data were analyzed with Beckman Coulter 32 Karat software version 5.0. Unless otherwise noted, linear gradients were conducted from 5% to 95% solvent B (0.1% TFA in HPLC grade acetonitrile) over solvent A (0.1% TFA in HPLC grade water) in 10 minutes with a flow rate of 0.7 mL min$^{-1}$. Subsequent chain elongation and average coupling yields were estimated by RP-HPLC using methods described previously by Jang et al. (supra).

Additional characterization of peptoid oligomers was conducted using Liquid Chromatography/Mass Spectrometry (LC/MS). All peptoids described herein were analyzed using an Agilent 1100 Series LC/MSD Trap XCT equipped with an electrospray ion source. All LC/MS experiments were preformed in positive ion mode. Unless otherwise stated, all analyses were performed on peptoids cleaved from resin without further purification.

Peptoid Synthesis:

Synthesis of peptoid oligomers was conducted on Rink Amide resin (Novabiochem, San Diego, Calif.), using a modification of the standard submonomer synthesis procedures described by Zuckermann et al. (supra). Peptoids were synthesized by manual techniques as well as automated procedures on a robotic workstation (Charybdis Instruments) with software program files written in house. All reactions were conducted on solid-phase at room temperature.

Typically, 100 mg of Rink Amide resin at a loading level of 0.55 mmol g$^{-1}$ was swollen in 3 mL of dichloromethane (DCM) for 45 minutes before Fmoc deprotection. Multiple washing steps using N,N'-dimethylformamide (DMF) (4×2 mL) and DCM (3×2 mL) were performed between each synthetic procedure described below. All reactant equivalents are based on resin loading level for a given amount of resin. Resin was Fmoc deprotected by treatment with 20% piperidine in DMF (15 mL g$^{-1}$ resin, 20 minutes). Deprotection reagents were washed from the resin and approximately 20 stoichiometric equivalents (eq) bromoacetic acid (1.2 M in DMF, 8.5 mL g$^{-1}$ resin) and 24 eq diisopropylcarbodiimide (2 mL g$^{-1}$ resin) were added. The bromoacetylation reaction mixture was agitated at room temperature for 20 minutes. Following washing, 20 eq monomer amine (1.0 M in DMF, 10 mL g$^{-1}$ resin) were added and the reaction was agitated for 20 minutes. Bromoacetylations and monomer amine displacements were repeated until peptoid oligomers of desired length were achieved.

Peptoid products were cleaved from solid support by treatment with 95% trifluoroacetic acid (TFA) in water (40 mL g$^{-1}$ resin) for 10 minutes. The TFA cleavage cocktail was evaporated under nitrogen. For characterization by RP-HPLC and LC/MS, peptoids were resuspended in 1 mL HPLC solvent (50% acetonitrile in water).

Polyfunctionalized Peptoid 24-mer (4):

Linear peptoid dodecamers were synthesized with high efficiency using techniques described above. Compound 1 was allowed to react with 21 eq phenyl propargyl ether (0.06 M), 40 eq CuI (0.11 M), 20 eq ascorbic acid (0.06 M) and 50 eq DIPEA (0.14 M) in 20 mL DMF/pyridine 7/3 v/v (0.2 mL mg$^{-1}$ resin) in a 20 mL scintillation vial (Wheaton Scientific, Millville, N.J.), generating compound 2. In order to completely dissolve the solid reactants, the vial was placed in a bath sonicator (VWR Aquasonic 75HT) and sonicated for 5-10 minutes. The vial was purged with gaseous nitrogen, tightly capped, sealed with Parafilm and shaken at room temperature for 18 hours. Following completion of the reaction, the resin was transferred to a 10 mL fritted syringe (Torviq) and washed with DMF (7×3 mL), Cu scavenger cocktail (DMF/pyridine 6/5 v/v, ascorbic acid 0.02 g mL$^{-1}$) (7×3 mL) and DCM (7×3 mL). The resin was then dried under nitrogen gas flow and approximately 3 mg was removed for characterization. Peptoid 2 was then elongated to a 24-mer (FIG. 1, Scheme 1, Compound 3) through twelve rounds of monomer amine addition as described above. Compound 3 was added to 21 eq benzyl azide (0.06 M), 40 eq CuI (0.11 M), 20 eq ascorbic acid (0.06 M) and 50 eq DIPEA (0.14 M) in 20 mL DMF/pyridine 7/3 v/v (0.2 mL mg$^{-1}$ resin) in a 20 mL scintillation vial. The vial was purged with gaseous nitrogen, tightly capped, sealed with Parafilm and was allowed to stir at room temperature for 18 hours, affording peptoid 4. Following washing steps, the generation of peptoid 4 was confirmed using RP-HPLC and LC/MS. Overall purity of peptoid 4 was found to be >35% as calculated by analytical RP-HPLC. Sequencing of peptoid 4 was conducted using a MS/MS fragmentation technique on an Agilent 1100 Series LC/MSD Trap XCT equipped with an electrospray ion source. LC/MS$^2$ experiments were performed in positive ion mode.

Synthesis of Multi-functionalized Peptoid Dodecamer (12):

Approximately 100 mg of peptoid 5-bound Rink Amide resin was swollen in DCM for 45 minutes. The DCM was removed and the swollen resin was transferred to a 20 mL scintillation vial. Depending on the hydrophobicity of the respective coupling partner, the resin was suspended in either 20 mL 2-butanol/DMF/pyridine 5/3/2 v/v/v (0.2 mL mg$^{-1}$ resin) or 20 mL DMF/pyridine 7/3 v/v (0.2 mL mg$^{-1}$ resin). To compound 5 was added 21 eq phenyl propargyl ether (0.06 M) along with 40 eq CuI (0.11 M), 20 eq ascorbic acid (0.06 M) and 50 eq DIPEA (0.14 M) to generate peptoid 6. In order to completely dissolve the solid reactants, the vial was placed in a bath sonicator (VWR Aquasonic 75HT) and sonicated for 5-10 minutes. The vial was purged with nitrogen, tightly capped, sealed with Parafilm and vigorously shaken at room temperature for 18 hours. Following completion of the reaction, the resin was transferred to a 10 mL flitted syringe (Torviq) and washed with DMF (7×3 mL), Cu scavenger cocktail (DMF/pyridine 6/5 v/v, ascorbic acid 0.02 g mL$^{-1}$) (7×3 mL), and DCM (7×3 mL). The resin was then dried under nitrogen gas flow and approximately 3 mg was removed for characterization.

Figure 2:
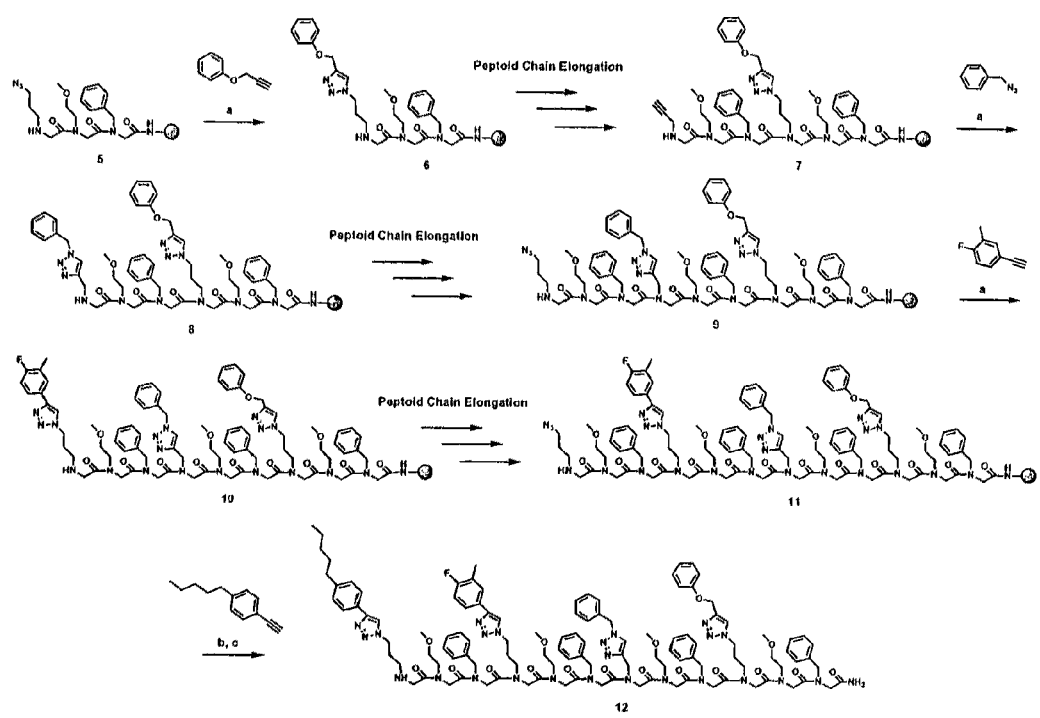
FIG. 2 (Scheme 2) shows sequential click chemistry performed on solid phase support. All coupling partners were present at 0.06 M. a) CuI (0.11 M), ascorbic acid (0.06 M) and DIPEA (0.14 M) in 2-butanol/DMF/pyridine (5/3/2 v/v/v), room temperature, 18 h. b) CuI (0.11 M), ascorbic acid (0.06 M) and DIPEA (0.14 M) in DMF/pyridine (7/3 v/v), room temperature, 18 h. c) 95% TFA in $H_2O$, room temperature, 10 min.

Resin-bound peptoid trimer 6 was elongated to a hexamer using techniques as described (FIG. 2; Scheme 2, Compound 7). Benzyl azide (0.06 M) was then coupled onto the terminal alkyne functionality of 7 using methods outlined above, generating compound 8. The click chemistry reagents were washed from the resin and a small amount of compound (3 mg) was removed for characterization. This sequential click chemistry reaction method was repeated until four complete rounds of elongation and cycloaddition had been achieved (FIG. 2; Scheme 2, Compound 12). Compound 12 was confirmed using RP-HPLC (FIG. 3) and MS/MS sequencing techniques.

Synthesis of Peptoid-ferrocene Conjugate (13):

Approximately 100 mg of Rink Amide resin was swollen in DCM for 45 minutes. The DCM was removed and the resin was Fmoc deprotected by treating it with 20% piperidine in DMF (15 mL g$^{-1}$ resin, 20 min). Deprotection reagents were washed from the resin and peptoid trimers were generated that contained two methoxyethylamine monomers and a terminal azidopropyl moiety. The resin was transferred to a 20 mL scintillation vial and ethynylferrocene (21 eq, 0.06 M), 40 eq CuI (0.11 M), 20 eq ascorbic acid (0.06 M) and 50 eq DIPEA (0.14 M) were added to the resin-bound peptoid in 20 mL 2-butanol/DMF/pyridine 5/3/2 v/v/v (0.2 mL mg$^{-1}$ resin). The vial was purged with nitrogen gas, sealed with Parafilm and shaken at room temperature for 18 hours. The click chemistry reagents were washed from the resin and a small amount of the peptoid-ferrocene conjugate was removed for characterization. This monofunctionalized peptoid trimer was then elongated to a hexamer with two additional methoxyethylamine monomers and a terminal azidopropyl moiety (Compound 14). The resin was transferred to a 20 mL scintillation vial and 17α-ethynylestradiol (21 eq, 0.06 M), 40 eq CuI (0.11 M), 20 eq ascorbic acid (0.06 M) and 50 eq DIPEA (0.14 M) were added to the resin-bound peptoid in 20 mL DMF/pyridine 7/3 v/v mL (0.2 mL mg$^{-1}$ resin). The vial was purged with nitrogen, tightly capped, sealed with Parafilm and shaken at room temperature for 18 hours. Following completion of the reaction, the resin was transferred to a 10 mL flitted syringe (Torviq) and washed with DMF (7×3 mL), Cu scavenger cocktail (DMF/pyridine 6/5 v/v, ascorbic acid 0.02 g mL$^{-1}$) (7×3 mL) and DCM (7×3 mL). The resin was then dried under nitrogen gas flow and approximately 3 mg was removed for characterization. Peptoid 13 was purified to >96% purity as calculated by RP-HPLC.

Electrochemical Analyses:

Ethynylferrocene (1.05 mg, 5.0 μmol was dissolved in 10 mL HPLC grade water. NaCl (29.22 mg, 0.5 mmol) was added to the solution as a supporting electrolyte. Similarly, solutions of 10 mL water, 6.3 mg (5.0 μmol peptoid 13 or 4.8 mg (5.0 μmol) peptoid 14 and 29.22 mg (0.5 mmol) NaCl were prepared. The following techniques were performed identically on 0.5 mM ethynylferrocene (50 mM NaCl), 0.5 mM 13 (50 mM NaCl) or 0.5 mM 14 (50 mM NaCl). Approximately 4 mL of solution was transferred to an electrochemical cell and subjected to cyclic voltammetry (CV) experiments. Cyclic voltammetry was conducted using a CH Instruments 600A Electrochemical Analyzer and CV curves were generated using software developed by CH Instruments. Current (μA) versus Potential (V) was measured across a freshly polished CHI104 3 mm diameter glassy carbon disk working electrode (CH Instruments) with a Ag/AgCl (3 M KCl) reference electrode (CH Instruments) and a Pt wire reference electrode (scan rate=9.0 mV s$^{-1}$).

Results

Experiments were initiated with the solid-phase synthesis of a linear peptoid dodecamer scaffold including three azidopropyl sidechains site-specifically positioned in the oligomer sequence (FIG. 1; Scheme 1, Compound 1). Peptoid scaffolds were synthesized with high efficiency on Rink Amide resin using standard "submonomer" synthesis protocols (Horn et al., *Bioconjugate Chem.*, 2004, 15, 428). Azide-functionalized sidechains were conveniently integrated as N-substituents in the peptoid sequence using 3-azido-1-aminopropane (Carboni et al., *J. Org. Chem.*, 1993, 58, 3736) as a submonomer reagent. Following synthesis and characterization of peptoid 1, the present inventors successfully conjugated phenyl propargyl ether to the three azide groups on the dodecamer scaffold. Trivalent conjugation was achieved by reacting 1 with phenyl propargyl ether in the presence of CuI, ascorbic acid and N,N'-diisopropylethylamine (DIPEA) in DMF/pyridine (7/3 v/v) at room temperature for 18 hours.

This reaction resulted in the formation of a 1,2,3-triazole linkage between the peptoid scaffold and the side chain conjugates (FIG. 1; Scheme 1, Compound 2).

The present inventors then investigated whether triazole linkages generated by click chemistry cycloadditions are compatible with peptoid chain extension (FIG. 1; Scheme 1, Compound 3). Following synthesis of 2, the click chemistry reagents were washed from the solid-phase and twelve complete peptoid monomer addition cycles were executed. In order to allow for azide coupling, three propargyl sidechains were incorporated into the 24-mer peptoid scaffold 3. Benzyl azide was conjugated to the three alkyne groups in a second round of click chemistry modification to generate 4. All products shown in FIG. 1; Scheme 1 were characterized and confirmed after each elongation and cycloaddition cycle using Reversed-Phase High Performance Liquid Chromatography (RP-HPLC) and Liquid Chromatography/Mass Spectrometry sequencing techniques (LC/MS"). Both azide and alkyne groups within the oligomer sequence were modified with equal efficiency (>95% conversion).

Figure 3:
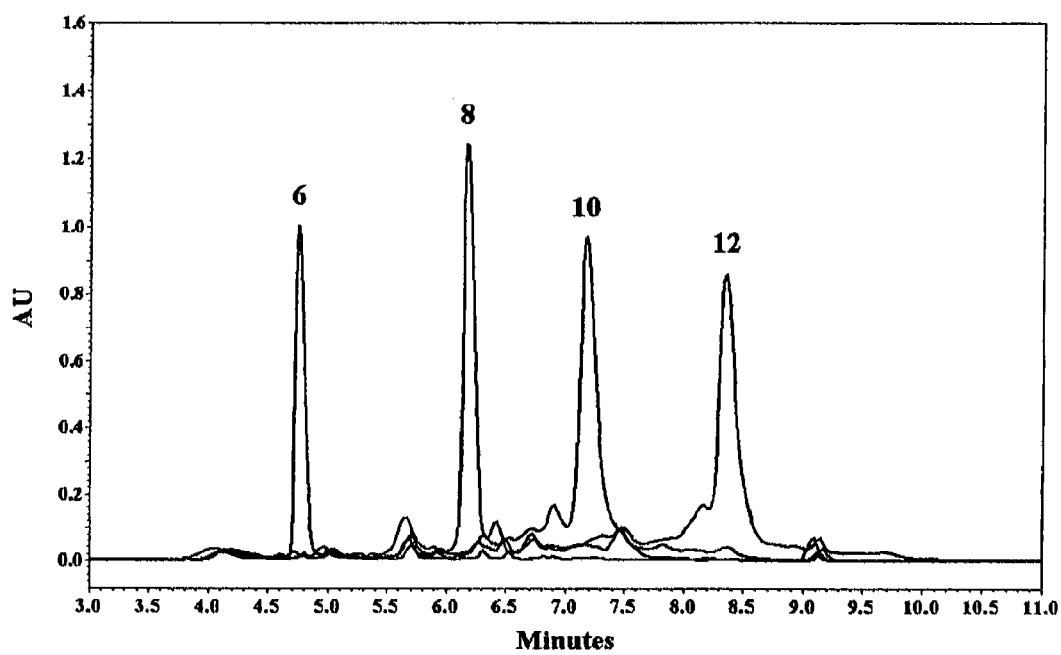
FIG. 3 depicts representative analytical RP-HPLC traces showing 6, 8, 10 and 12 following cleavage from solid support. Chromatographic analysis was performed on each of the crude products and is shown as overlaid traces.

Using this approach, the present inventors successfully generated multi-functionalized peptoid dodecamers that had been extended and modified through four sequential cycles of click chemistry (FIG. 2; Scheme 2). Peptoid trimers containing terminal azide functionalities (FIG. 2; Scheme 2, Compound 5) were synthesized on solid-phase support. Compound 6 was generated by reacting 5 with phenyl propargyl ether in the presence of CuI, ascorbic acid and DIPEA in 2-butanol/DMF/pyridine (5/3/2 v/v/v) at ambient temperature for 18 hours. The click chemistry reagents were washed from 6 and three complete rounds of peptoid monomer addition were conducted, generating peptoid hexamer 7. Benzyl azide was allowed to react with 7 in a second cycle of click chemistry to afford peptoid 8. The technique of sequential elongation and cycloaddition was repeated until peptoid dodecamers comprising four distinct side chain conjugates attached at sites specifically modified for incorporation were synthesized. Standard submonomer extension of peptoids 8 and 10 afforded peptoids 9 and 11, respectively. Peptoids 10 and 12 were synthesized through the conjugation of 4-ethynyl-1-fluoro-2-methylbenzene and 1-ethynyl-4-pentylbenzene onto peptoids 9 and 11, respectively. FIG. 3 shows overlaid analytical RP-HPLC spectra of crude intermediates 6, 8, 10 and product 12 following cleavage from solid-phase support. All products shown in FIG. 2; Scheme 2 were characterized and confirmed after each elongation and cycloaddition cycle using RP-HPLC and LC/MS$^2$ sequencing. All azide and alkyne-containing coupling partners in FIG. 2; Scheme 2 were conjugated with their respective alkyne and azide reactive sites on the oligomer scaffold with high efficiency (>95% conversion). The overall crude purity of final product 12 was found to be >75% as evaluated by RP-HPLC (FIG. 3, Trace 12).

Figure 4:
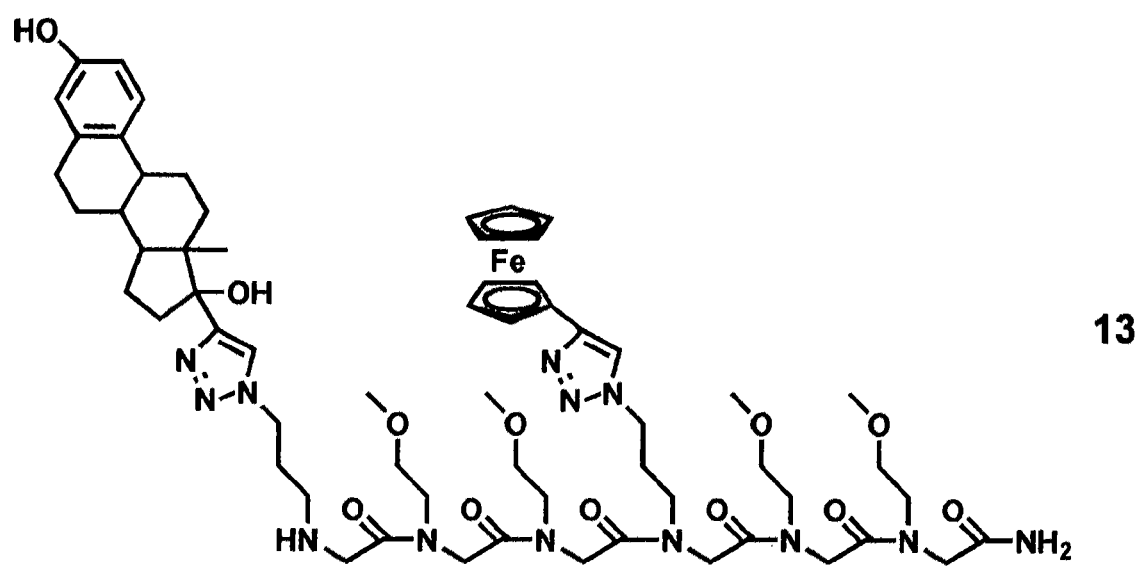
FIG. 4 shows the structure of a water-soluble bi-functionalized peptoid hexamer generated for biosensor applications.

The feasibility of using the sequential click chemistry method to integrate multiple constituents suitable for the development of peptoids as biosensor platforms was also explored. This involved selection of a sensor moiety and a bioactive ligand as groups for conjugation. The reversible redox properties of ferrocene/ferrocenium have previously been exploited for biosensor applications (Casas-Solvas et al., *Org. Lett.* 2004, 6, 3687; Forrow et al., *Bioconjugate Chem.*, 2004, 15, 137; Zhang et al., *J. Am. Chem. Soc.*, 2005, 127, 10590). Additionally, estradiol is a typical representative of a class of clinically important hormone ligands, leading to the study of estradiol conjugates for biomedical applications (Blizzard et al., *Biorg. Med. Chem. Lett.*, 2005, 15, 3912). Reports have shown that stable organometallic hormone pharmacophores can be generated using a 17α-(ferrocenylethynyl)estradiol complex (Osella et al., *Helv. Chim. Acta*, 2001, 84, 3289). Utilizing the sequential click chemistry method, peptoid 13 (FIG. 4) was generated as a prototype sensor platform in which ethynylferrocene and 17α-ethynylestradiol were site-specifically positioned along the oligomer scaffold. Methoxyethyl groups were incorporated as the predominant sidechain in 13 in order to increase overall molecular hydrophilicity and impart water solubility to a compound incorporating two hydrophobic moieties.

Figure 5:
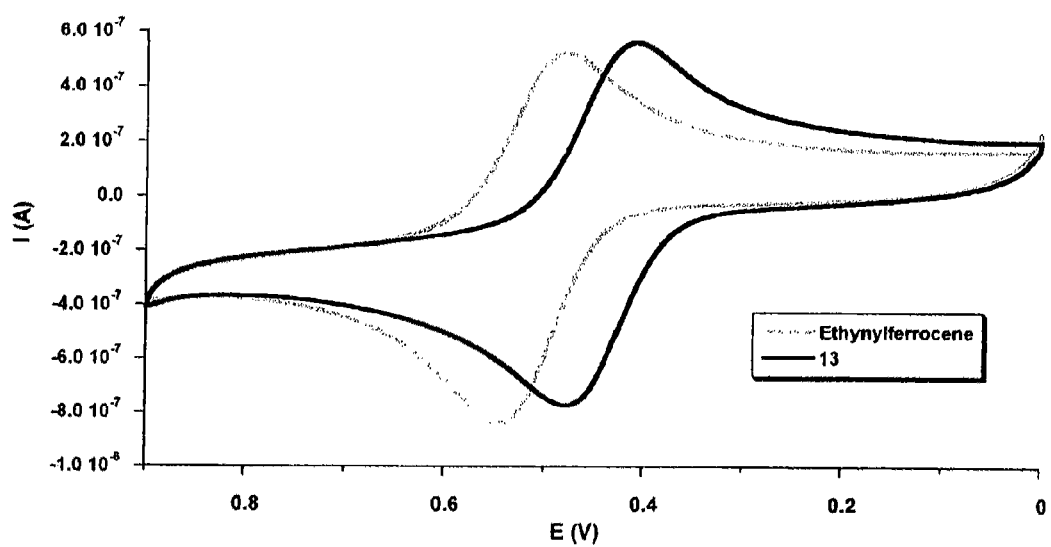
FIG. 5 shows cyclic voltammetry curves of ethynylferrocene (0.5 mM) and 13 (0.5 mM) in water with NaCl (50 mM) as supporting electrolyte, a glassy carbon working electrode, Ag/AgCl reference electrode and a Pt wire counter electrode with a scan rate at 9.0 mV $s^{-1}$.

To test the effect of triazole conjugation on ferrocene redox properties, compound 13 was purified to >96% as determined by RP-HPLC and the electrochemical behavior of ethynylferrocene and 13 were compared using cyclic voltammetry (CV). Additionally, the influence of the estradiol group on the redox potential of the neighboring ferrocene moiety was evaluated by comparing the electrochemical characteristics of 13 with its azido-functionalized precursor 14. CV experiments were carried out at room temperature using previously described methods (Casas-Solvas et al., *Org. Lett.* 2004, 6, 3687). CV was performed on solutions of ethynylferrocene (0.5 mM), 13 (0.5 mM) or 14 (0.5 mM) prepared in water with NaCl (50 mM) as a supporting electrolyte, using a Ag/AgCl (KCl 3 M) reference electrode, a freshly polished glassy carbon working electrode, and a Pt wire counter electrode with a scan rate of 9.0 mV s$^{-1}$. Cyclic voltammograms of ethynylferrocene and 13 showed reversible redox couples of ferrocene/ferrocenium, as shown in FIG. 5. The values of the formal redox potential ($E^0$) and the half-peak potential ($E_{p/2}$) of ethynylferrocene, 13 and 14 are shown in Table 1. As expected, the ferrocene core of 13 showed a significant decrease in redox potential when compared to ethynylferrocene. This is attributed to the altered electronic environment established by the extended conjugation of the ferrocene cyclopentadiene group with the 1,2,3 triazole ring (Rose et al., *Inorg. Chem.* 1993, 32, 781). Interestingly, $E^0$ and $E_{p/2}$ values for 13 and 14 were very similar, indicating that the redox potential of the ferrocene group is not affected by conjugation of a proximal bulky substituent. Because it is desirable to retain a similar relative signal intensity between sensor molecules that contain a variety of bioactive ligands, it is advantageous that the electrochemical properties of the conjugated ferrocene are not substantially diminished by the neighboring estradiol. Future studies will investigate the development of electrochemical-based biosensors in which site-specifically positioned sensor groups are used to report a change in redox potential upon protein binding by suitably modified peptoid oligomers (Plumb et al., *Bioconjugate Chem.*, 2003, 14, 601).

TABLE 1

| Table 1 Electrochemical Data by Cyclic Voltammetry$^a$ | | |
|---|---|---|
| Entry | $E^o$ (V) | $E_{p/2}$ (V) |
| Ethynylferrocene | 0.512 | 0.525 |
| 13 | 0.442 | 0.459 |
| 14 | 0.442 | 0.456 |

$^a$Cyclic voltammetry experiments were conducted on ethynylferrocene (0.5 mM), 13 (0.5 mM) or 14 (0.5 mM) in water with NaCl (50 mM) as supporting electrolyte, a glassy carbon working electrode, Ag/AgCl reference electrode and a Pt wire counter electrode with a scan rate at 9.0 mV s$^{-1}$.

EXAMPLE II

The present invention is directed to a novel method for generating compounds for polyvalent display. In particular, the present inventors describe an implementation that allows synthesis of relatively inexpensive and biologically relevant hormone-dependent agents that exhibit significant advantages over those previously described in the literature. Peptidomimetic scaffolds outfitted, for example, with multiple 17α-ethynylestradiol and ferrocene functionalities can be generated with minimal effort and cost. See FIG. 6, wherein a general method for synthesis of polyvalent selective hormone receptor cytotoxic agents is shown. Triazole linkages between the ligand and scaffold are formed in highly regiospecific, thermodynamically favorable conjugation reactions that occur at room temperature in organic or aqueous solvents. Furthermore, the scaffolds used are N-substituted glycine oligomers (peptoids), which may prove beneficial in vivo due to their enhanced resistance to proteolytic degradation.

The oligomers shown, for example, in FIG. 7 may be utilized as in vitro selective hormone receptor cytotoxic agents to inhibit cell proliferation in breast cancer cell lines. Such cell-based assays are useful for evaluating the potential efficacy of the polyvalent selective hormone receptor cytotoxic agents of the present invention. In one embodiment, the selective hormone receptor cytotoxic agents may be tested for therapeutic efficacy by contacting MCF-7/Her 2 breast cancer cells with compounds 1-3 to determine 1) if these compounds bind to estrogen receptors of MCF-7/Her 2 breast cancer cells and 2) to measure cellular proliferation and/or cytotoxicity in the presence of compounds 1-3 to determine if these compounds impart cellular toxicity upon binding. It is predicted that displaying selective hormone receptor agonists in a multivalent arrangement will allow for increased binding avidity of compounds 1-3, enhancing their overall selectivity and therapeutic effect. Additionally, with respect to the polyvalent display of ferrocene on compounds 2 and 3, cytotoxic effects can be evaluated as a function of local ferrocene concentration. The anti-proliferative effects of compounds 1-3 will be compared to existing selective estrogen modulator therapies presently in use, such as ferrocifen.

The structures of the following ethynyl-steroid conjugates are presented as exemplary bioconjugates that may be utilized in the generation of hormone-dependent cytotoxic agents using the methods of the present invention.

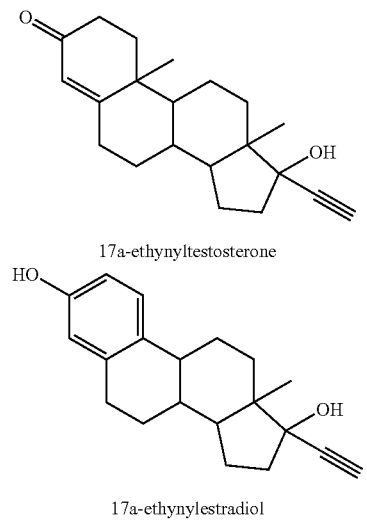

17a-ethynyltestosterone 17a-ethynylestradiol

-continued

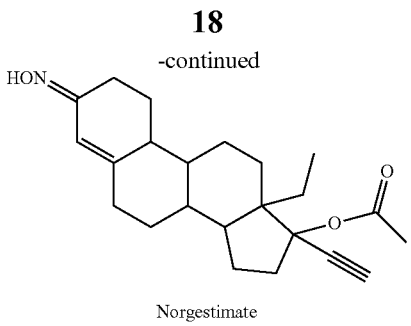

Norgestimate

EXAMPLE III

Additional applications of the invention include the synthesis of molecules with high affinity for a variety of biological targets, which exhibit such high affinity as a consequence of the polyvalent display of select conjugated binding groups on a linear oligomeric scaffold. The term polyvalency is used herein to refer to high-affinity binding between surfaces wherein the affinity is conferred at least in part by the binding of repeated epitopes. It is noteworthy that polyvalency is a defining characteristic of the surfaces of almost all invading pathogens. In addition, other applications include highly potent pharmaceuticals, whose therapeutic activity is anticipated to be enhanced due to the multiple presentation of cytotoxic moieties. Important applications in the field of biosensors, diagnostic agents, and molecular imaging probes are also encompassed by the present invention.

Targeting Viral Pathogens:

Viral molecules, particularly those displayed on a viral capsid, are excellent targets against which to design polyvalent linear oligomers of the present invention which comprise heterogeneous pendant groups. Binding pairs comprising viral "ligands" and the cell surface moieties with which they interact are known for a variety of viruses and cellular targets. Viruses can bind to almost all classes of molecules on cellular surfaces, including: sugars (polyoma and orthomyxoviruses, for example, recognize sialyloligosaccharides); phosphatidyl lipids (vesicular stomatitis virus (VSV), for example, recognize phosphatidylserine and phosphatidylinositol); and proteins (HIV recognizes CD4; human rhinovirus recognizes intercellular adhesion molecule-1, ICAM-1). For a review, see Mammen et al., *Angew. Chem. Int. Ed.*, 1998, 37, 2754 and Kiessling et al., *Angew. Chem. Int. Ed.* 2006, 45, 2348, which are incorporated herein by reference.

The influenza virus, for example, is known to attach to the surface of bronchial epithelial cells via interaction between multiple trimers of the lectin hemagglutinin (HA), which is densely packed on the surface of the virus, and multiple moieties of N-acetylneuraminic acid [sialic acid (SA)], the terminal sugar on many glycoproteins. See Mammen et al. (supra). In view of the above, it is envisioned that the method of the present invention may be used to design polyvalent viral ligand-dependent cytotoxicity agents. Such agents would comprise a pendant group or bioconjugate designed to interact with, for example, HA on the influenza virus and a cytotoxic moiety, such as those described herein and known in the art. Bioconjugates may be modeled to mimic the structure of SA as it is presented as a terminal sugar.

Targeting Bacterial Pathogens:

A variety of binding pairs comprising bacterial proteins and cell surface proteins are known in the art and discussed in Mammen et al. (supra). In general, bacteria bind either directly to a cell surface molecule or moiety, or to molecules in the extracellular matrix of preferred tissues. Moreover, bacterial molecules have been identified that bind to both sugars and proteins. Uropathogenic *E. coli* strains, for example, are known to attach both directly and indirectly to the surface of epithelial cells in the urethra and bladder via polyvalent interactions. Several bacterial surface proteins have been identified that confer this tissue specificity, including: P-fimbrae (containing protein G) and type I fimbrae (containing the FimH adhesin). The lectin-like protein G, which is localized on the tips of P-fimbrial filaments of uropathogenic bacteria, adheres to multiple copies of the Gal(a1, 4)Gal (PK antigen) portion of a glycolipid expressed on the surface of epithelial cells in the urinary tract, especially the kidney. Multiple copies of *E. coli* F-protein attach polyvalently to fibronectin, a soluble glycoprotein which can bind polyvalently to the surface of epithelial cells. As a result of these polyvalent interactions, and potentially others, the *E. coli* collect and proliferate in tissues of the urinary tract, wherein they can cause disease, such as pyelonephritis.

It is, therefore, envisioned that the method of the present invention may be used to design polyvalent bacterial ligand-dependent cytotoxicity agents. Such agents would comprise a pendant group or bioconjugate designed to interact with either bacterial protein G or F-protein, for example, on bacterial cells and a cytotoxic moiety, such as those described herein and known in the art. Alternatively, an oligomer of the present invention may be synthesized that displays pendant groups that interact with bacterial protein G, pendant groups that interact with bacterial F-protein, and at least one conjugated cytotoxic moiety. Bioconjugates for protein G interactors may be modeled to mimic the structure of the Gal(a1,4)Gal (PK antigen) portion of a glycolipid expressed in the urinary tract. Bioconjugates for F-protein interactors may be modeled to mimic the structure of the F-protein binding sites on fibronectin.

Targeting Cell-Cell Interactions:

Under some circumstances, it is desirable to reduce or inhibit interactions between cells. One such example involves platelet binding to arterial endothelial cells which can contribute to thrombotic events. In accordance with the present invention, polyvalent linear oligomers can be synthesized that comprise two or more pendant groups that specifically bind to thrombogenic vascular wall proteins. Such polyvalent linear oligomers can be used therapeutically to block acute platelet deposition at sites of vessel injury by molecularly masking thrombogenic vascular wall proteins. Arterial injury can result from a variety of natural events and invasive procedures, including angioplasty.

Potent Pharmaceuticals:

Polyvalent oligomers comprising a plurality of pendant groups, wherein the conjugated pharmaceutical moieties include two or more such moieties are also envisioned. The structures of several azidonucleosides are presented herein as exemplary bioconjugates that may serve as potent pharmaceuticals, particularly when presented multiply on an oligomeric scaffold.

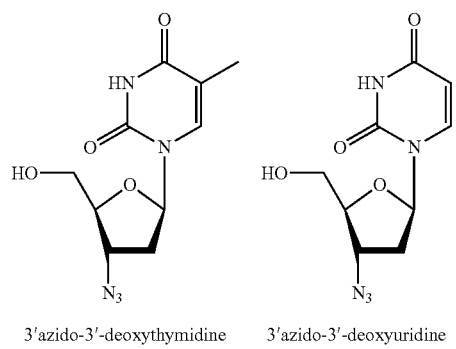

3'azido-3'-deoxythymidine    3'azido-3'-deoxyuridine

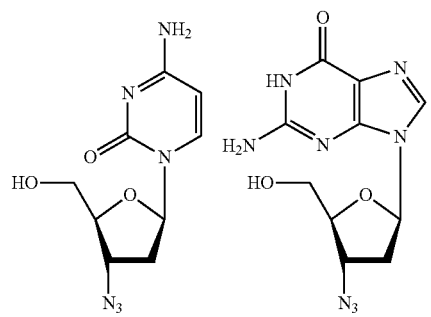

3'azido-3'-deoxycytidine    3'azido-3'-deoxyguanidine

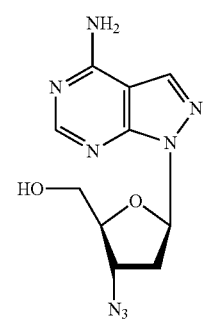

3'azido-3'-deoxyadenine Analogue

The present invention also encompasses polyvalent oligomers comprising a plurality of pendant groups, wherein the pendant groups are antibiotic moieties comprising the active site(s) of a desired antibiotic or antibiotics. Such polyvalent antibiotics are anticipated to act as potent antibiotics by virtue of their polyvalent presentation of antibiotic moieties. Polyvalent oligomers comprising a plurality of antibiotic moieties conjugated as pendant groups may comprise multiple copies of antibiotic moieties of a single antibiotic or multiple copies of antibiotic moieties of different antibiotics. Polyvalent oligomers comprising multiple copies of antibiotic moieties of a single antibiotic are anticipated to exhibit enhanced potency. Polyvalent oligomers comprising multiple copies of antibiotic moieties of different antibiotics are likely to exhibit both enhanced potency and an expanded spectrum of activity. As such, polyvalent oligomers of the invention comprising a plurality of antibiotic moieties conjugated as pendant groups may prove to be efficacious at lower doses as compared to those required for standard "monovalent" antibiotics due to their multivalency which, in turn, enhances potency.

Biosensors, Diagnostic Agents, and Molecular Imaging Probes: The methods of the present invention are also well suited to the synthesis of novel polyvalent oligomers comprising more than one type of pendant group, wherein the conjugated pendant group confers upon the oligomer the ability to function as a detector for the presence and/or activity of a particular molecule. Such functional groups include, but are not limited to: fluorophores, chelates, radioisotopes, affinity tags, and numerous other groups known to skilled practitioners (G. T. Hermanson, *Bioconjugate Techniques*, Academic Press: San Diego, Calif., 1996). To enhance the versatility of such polyvalent oligomers, different functional groups that interact with each other in a detectable manner can be conjugated to the same oligomeric backbone. Such groups may confer a detectable signal when they are, for example, brought within a certain proximity, perhaps as a consequence of a conformational change in a molecule to which the polyvalent oligomer has bound.

EXAMPLE IV

In another aspect, the method of the present invention may be used to synthesize polyvalent molecules comprising multiple copies of identical conjugated pendant groups on a linear oligomeric scaffold. Exemplary pendant groups for conjugation to a linear oligomeric scaffold of the present invention are presented herein above. A skilled practitioner would, however, be capable of envisioning other pendant groups of utility based on the teaching of the present invention. Such polyvalent molecules are anticipated to exhibit enhanced properties as a result of their polyvalent nature. With respect to polyvalent oligomers that present multiple copies of therapeutic moieties, such polyvalent molecules are likely to display dramatically improved therapeutic efficacy relative to their "monovalent" counterparts.

As described herein, an efficient protocol to effect multi-site conjugation reactions to oligomers on solid-phase support is presented. Sequence-specific N-substituted glycine "oligopeptoids" were utilized as substrates for azide-alkyne cycloaddition reactions. Diverse groups, including nucleobases and fluorophores, were conjugated at up to 6 positions on these peptoid sidechains with yields ranging from 88% to 96%. This strategy is broadly applicable for generating polyvalent displays on oligomeric backbones and allows precise control of spacing between pendant groups attached thereto.

Figure 10:
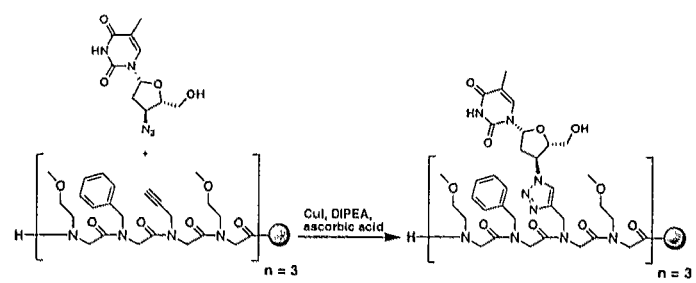
FIG. 10 shows a graphical abstract of aspects of the present method.
Figure 11:
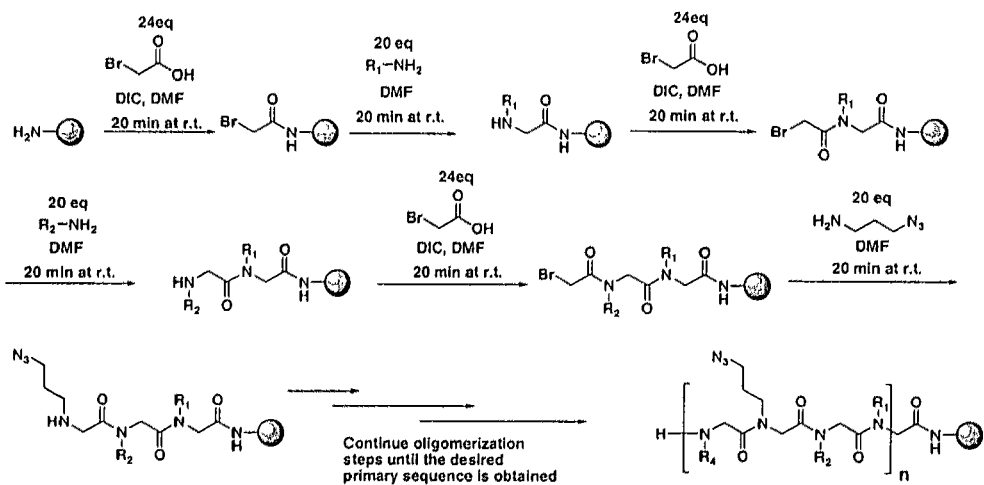
FIG. 11 shows a postoligomerization modification protocol.
Figure 11:
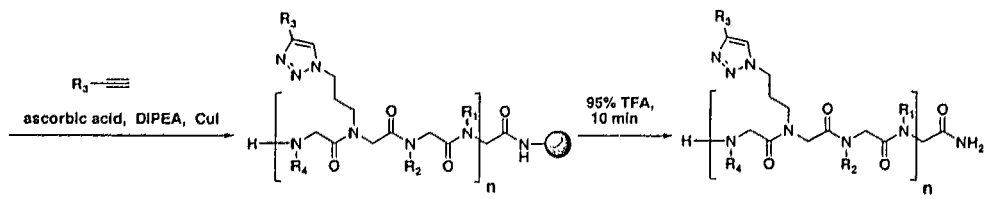
Figure 12:
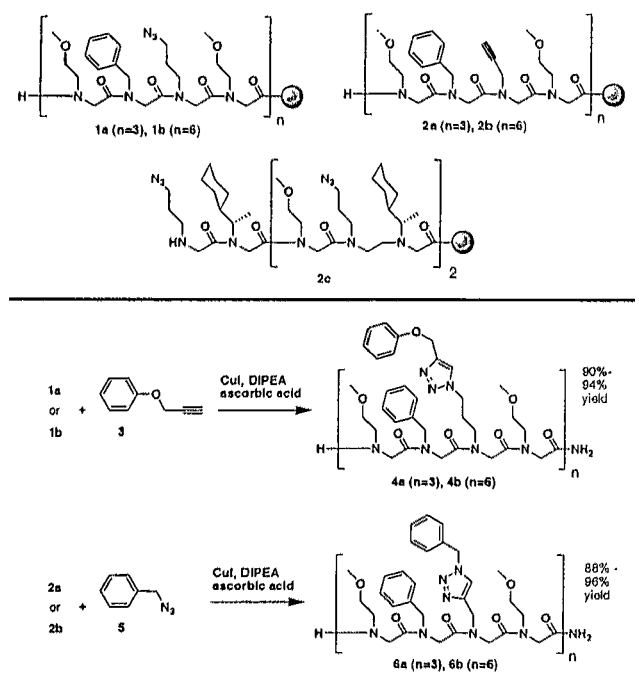
FIG. 12 shows postoligomerization modifications to pendant groups by regiospecific azide-alkyne [3+2] cycloaddition.

As indicated above, the strategy entails the synthesis of linear peptoid sequences including multiple reactive groups at specific sidechain positions (FIGS. 10 and 11). Peptoids were conveniently synthesized by standard "submonomer" automated protocols. Azide or alkyne functional groups were readily incorporated using 1-azido-3-aminopropane or propargylamine as submonomer reagents, affording oligomers 1a-2c on solid phase support. Corresponding alkyne or azide partners, respectively, were conjugated to these selectively reactive sites on the peptoid scaffolds (FIG. 12).

To demonstrate the broad utility of this reaction, diverse coupling partners were employed (Table 2). PRODAN, or 6-propionyl-2-(dimethylamino)naphthalene is a solvatochromic fluorophore that has proven useful as probe in biological systems. The present inventors conjugated the 6-azido-acetyl analog 7 to three sites on the peptoid scaffold 2a and synthesized a trivalent peptoid fluorophore 8 (Table 2, entry 1).

A trivalent peptoid-nucleoside conjugate 10 was similarly synthesized using azidothymidine 9 (Table 2, entry 2). Nucleobase conjugation to peptoid scaffolds at multiple residues offers a new type of synthetic oligomer similar to peptide nucleic acids for use as novel probes and diagnostic agents.

Peptoid trimers 11 to three positions on a helical peptoid[2b] octamer 2c, constructing a trivalent display 12 (Table 2, entry 3). This complex molecule was generated by a convergent "one-step" reaction, demonstrating the capability of click chemistry to efficiently generate elaborate branched architectures.

TABLE 2

Synthesis of Trivalent Conjugates on Peptoid Scaffold

| entry | coupling partners | scaffolds | product | conditions[a] |
|---|---|---|---|---|
| 1 | (structure 7) | 2a | 8 | A |
| 2 | (structure 9) | 2a | 10 | A |

TABLE 2-continued
Synthesis of Trivalent Conjugates on Peptoid Scaffold
| entry | coupling partners | scaffolds | product | conditions[a] |
|---|---|---|---|---|
| 3 | 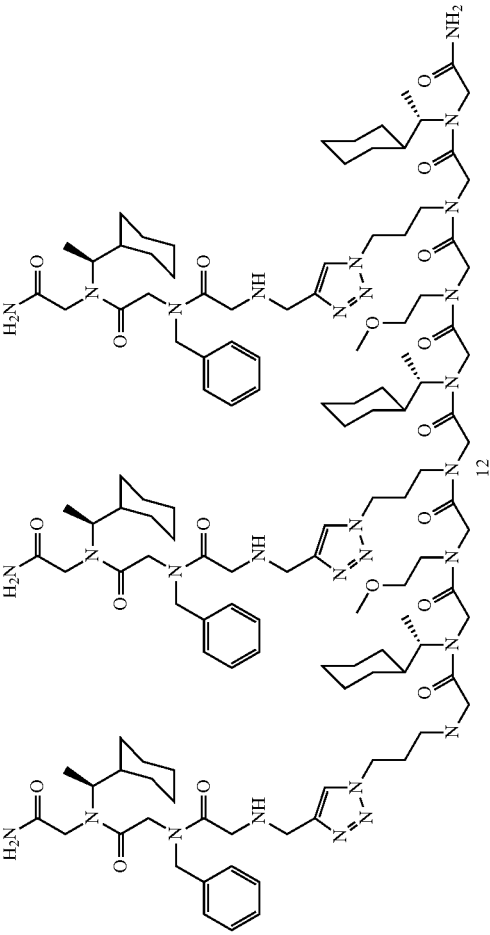 | 2c | 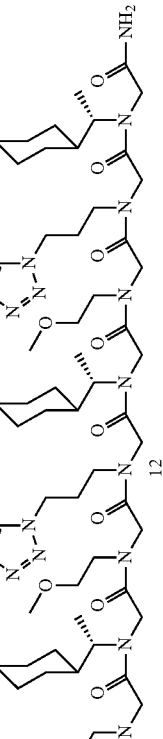 | B |

Prior to the present invention, sodium ascorbate or tris(carboxyethyl)phosphine were used for in situ reduction of Cu(II) salts in aqueous systems. As indicated herein, the present inventors demonstrate that Cu(I) salts can be used directly without complications in organic solvent systems, when stabilized by ascorbate in the presence of DIPEA. Reactions are conducted without: the formation of undesired by-products, the necessity for prior preparation of Cu(I) ligands, or the need for rigorous exclusion of oxygen. Indeed, the present inventors have successfully utilized ascorbic acid in a variety of organic solvent systems including pyridine, DMF and alcohols, underscoring the compatibility of this method with diverse solid phase resins. Thus, at low cost and remarkable convenience, these procedures can be incorporated into common solid phase organic synthesis protocols, potentially allowing seamless utilization in automated synthesizers.

As alluded to herein above, the polyvalent display of therapeutic moieties as conjugates displayed on oligomeric backbones offers the potential for the generation of super potent polyvalent therapeutic and/or prophylactic pharmaceuticals. Such polyvalent pharmaceuticals may be administered to subjects in need thereof alone or in the form of a composition further comprising a physiologically acceptable excipient. A skilled practitioner would be able to identify subjects for whom such administration would confer benefit and would, moreover, be able to determine suitable doses for administration based on a number of parameters (e.g., disease afflicting the patient, weight, age and condition of the patient).

Figure 13A:
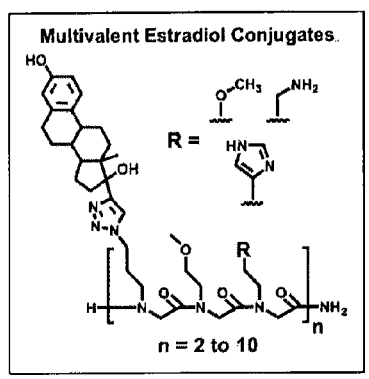
FIGS. 13A and B pictorially depict multivalent estradiol conjugates (A) and a hexavalent peptoid estradiol conjugate (B).
Figure 13B:
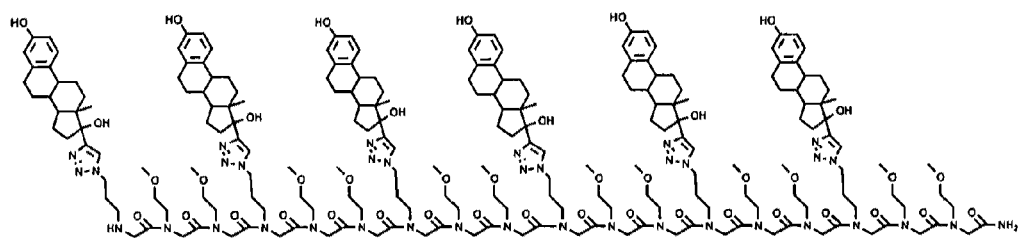

Exemplary polyvalent therapeutic oligomers of the present invention include estradiol-containing peptides, which are shown below as mono-, di-, trivalent conjugates. A hexavalent estradiol-peptoid conjugate is shown in FIG. 13B.

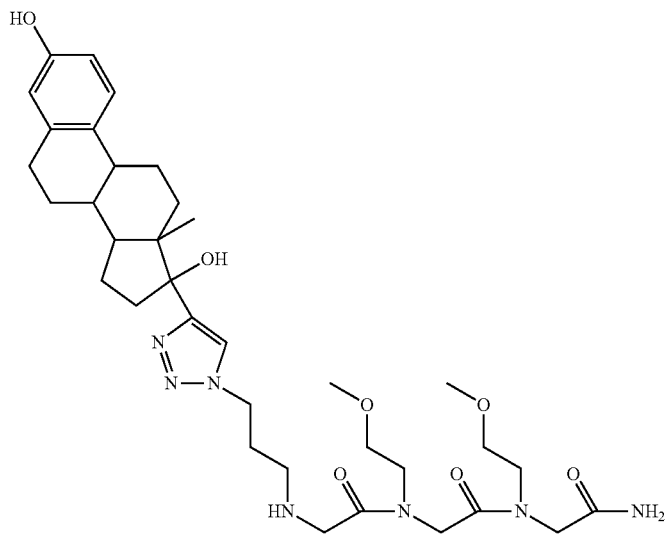

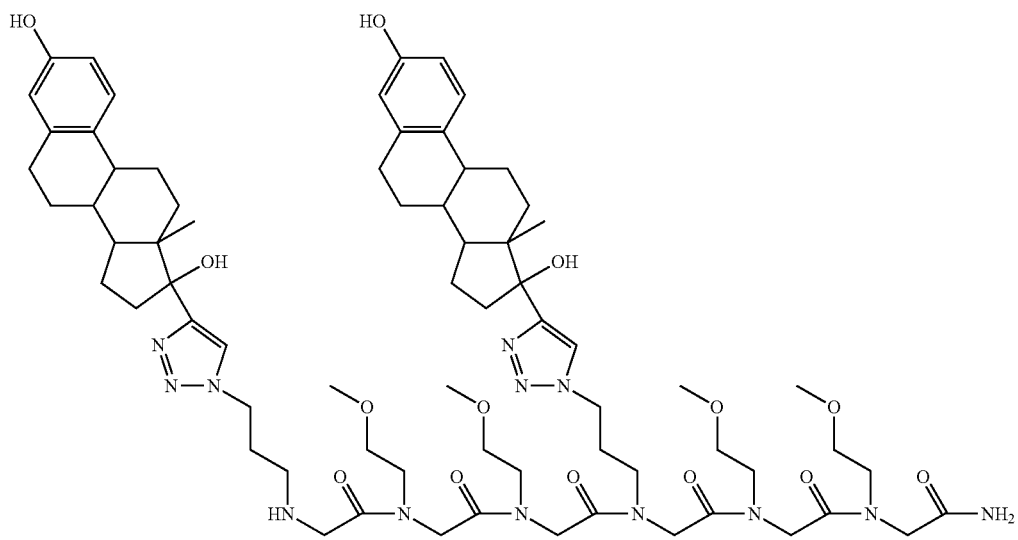

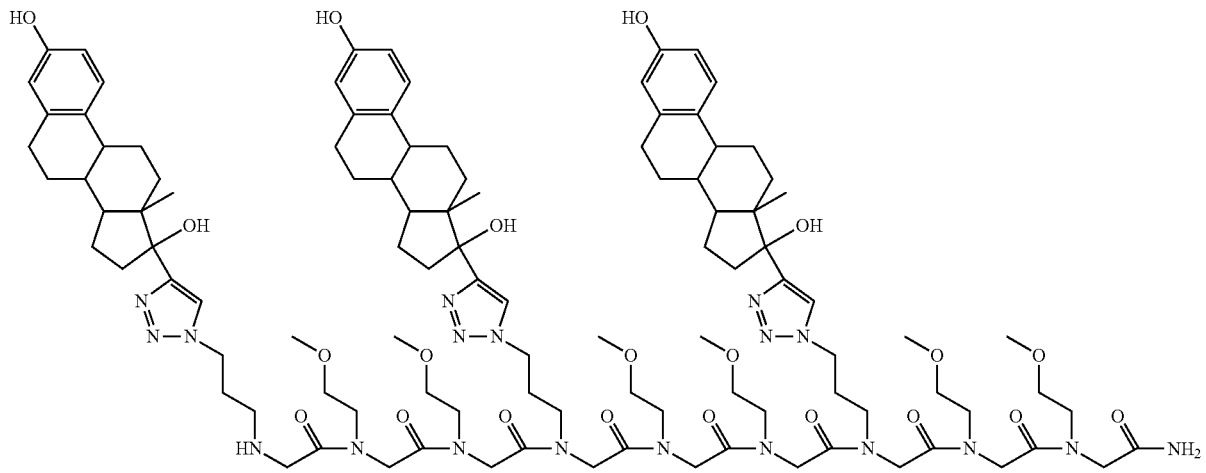
The following structure shows an estradiol-peptoid conjugate comprising a poly-Arg tail:
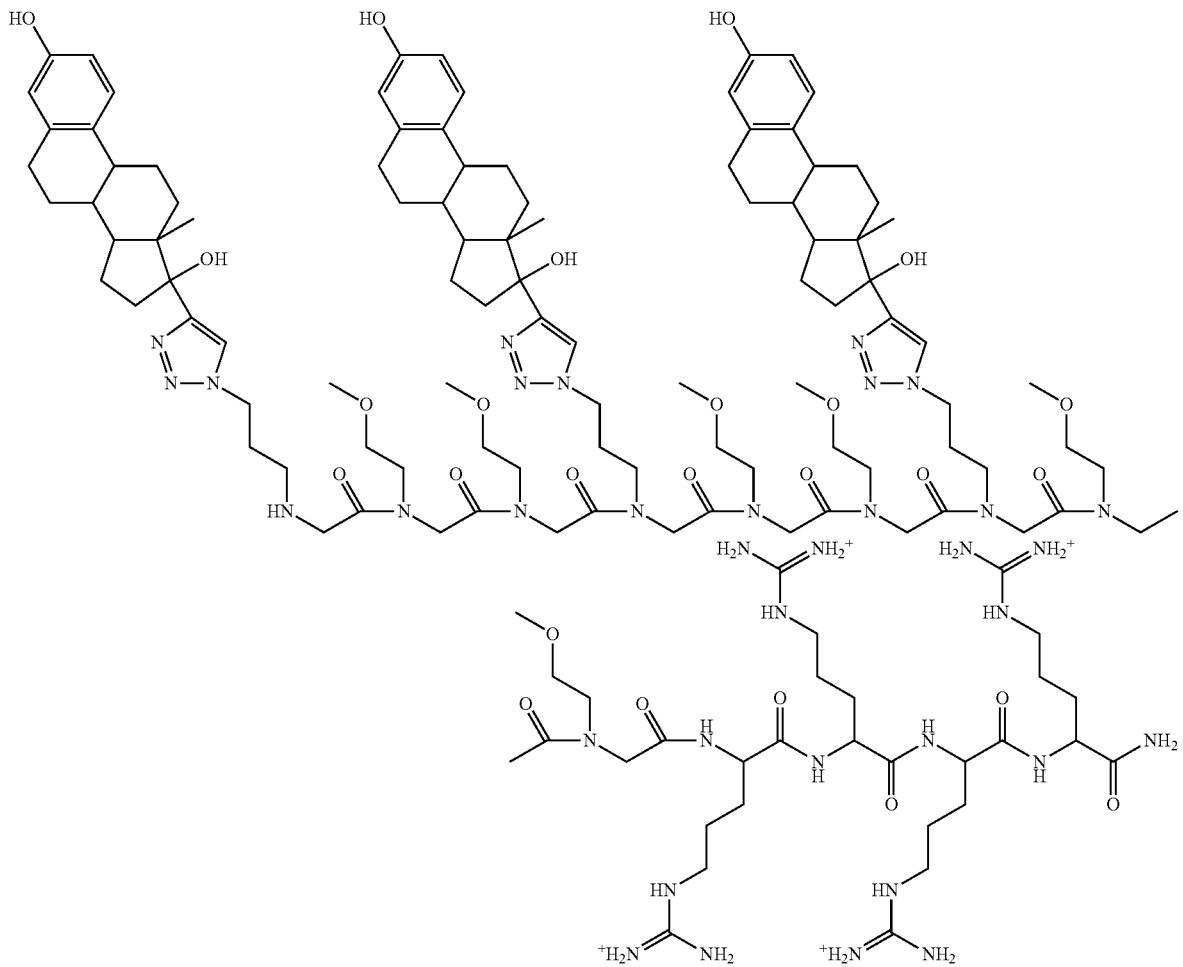

EXAMPLE V

Polyvalent Display of Peptides on a Peptoid Scaffold

Figure 8:
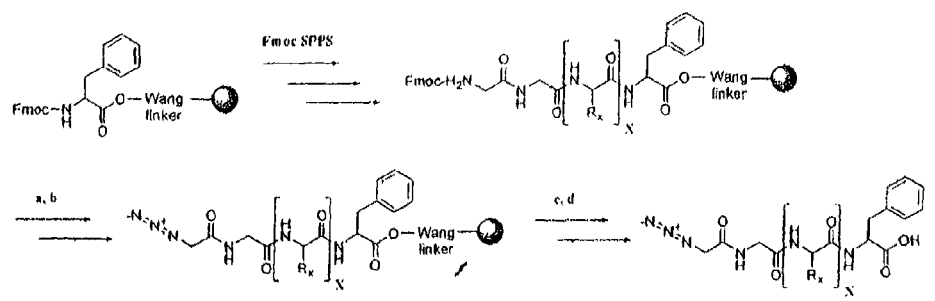
FIG. 8 (Scheme 4) shows a general method for polyvalent display of peptides on a peptoid scaffold.

FIG. 8 (Scheme 4) shows a hypothetical solid phase synthesis of a peptide oligomer in which the N-terminus amine has been converted to an azido group. The first steps show the solid-phase peptide synthesis (SPPS) of the primary peptide sequence. In step "a", F-moc deprotection is performed with 20% piperidine (base) in N-methyl-2-pyrrolidone (NMP). This step is followed by azide functionalization (step "b") by treating the resin-bound oligomer with trifluoromethylsulfonyl azide (CF3SO2-N3) in the presence of copper sulfate (CuSO4) in dichloromethane/methanol (9/1 v/v) at ambient temperature for 16 hrs. Finally, in steps "c" and "d", respectively, the peptide is cleaved from the resin with trifluoroacetic acid (TFA) (50% in DCM) and washed with 0.02M diethyldithiocarbamic acid sodium salt. See also Rijkers et al., 2002, Tet. Letters 43, 3657.

Butynoic acid can also be coupled to the end of a growing peptide sequence using standard coupling procedures. This coupling step may be used to render the peptide chain "clickable." Such coupling procedures may be used to advantage in generating peptoid-peptide hybrids, for example. A structure of butynoic acid is shown below:

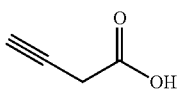

Figure 9:
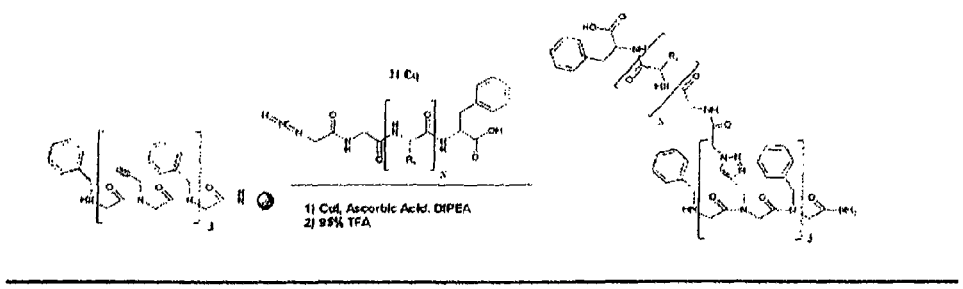
FIG. 9 (Scheme 5) shows a general method outlining the click chemistry procedure to polyvalently display the azido peptides on a peptidomimetic scaffold.

FIG. 9 (Scheme 5) outlines the click chemistry procedure of the present invention whereby azido peptides may be polyvalently displayed on a peptidomimetic scaffold. Equivalents are to be optimized through experimental results, but a good starting point is envisioned to utilize 40 eq Cu, 20 eq ascorbic acid, and 50 eq DIPEA. The cleavage shown in step 2 is achieved via treatment of the resin with 95% TFA in water for 10 min.

EXAMPLE VI

Multivalent Estradiol-Peptidomimetic Conjugates

Using the technology described herein, the present inventors have generated a versatile new class of multivalent hormone conjugates for selectively modulating the activity of estrogen receptors (ER), which are among the most important therapeutic targets in breast cancer. See FIG. 13, wherein one of the multivalent estradiol-peptidomimetic conjugates, a hexavalent peptoid estradiol conjugate is depicted.

Estrogen hormones such as 17β-estradiol (E2) are known to play a critical role in the development and progression of many human breast cancers (Thomas et al., Curr. Canc. Drug Tar., 2004, 4, 483). E2 is a natural ligand for ERα and ERβ, which have classically been described as nuclear receptors. In this role, ligand-activated ER functions via "genomic" pathways following nuclear localization by altering the extent of target gene transcription. In addition, estrogens are now also known to exhibit rapid effects via membrane-associated receptors that can trigger a set of "nongenomic" pathways, such as kinase cascades (Acconcia et al., Cancer Letters, 2006, 238, 1). The relationship between the genomic and non-genomic pathways is poorly understood. Further elucidation of the varying mechanisms of estrogen action is a priority for enhancing knowledge of breast cancer pathogenesis and molecular pharmacology. One promising approach is to develop estrogenic ligands that are capable of selectively activating a specific pathway. Macromolecular forms of estradiol, such as E2 conjugated to BSA protein, for example, have been prepared in studies that aim to activate the membrane-associated ER exclusively (Stevis et al., Endocrinology, 1999, 140, 5455). The stability and activity of estrogen-protein conjugates is highly variable, however, underscoring the need for optimized macromolecular estrogen conjugates (Harrington et al., Mol. Endocrinol., 2006, 20, 491).

To address this need, the present inventors have developed biomimetic polymers as a scaffold for a family of compounds that can be tailored to selectively modulate genomic or nongenomic ER pathways. In accordance with the present invention, the inventors have used "click chemistry" reactions to generate several compounds bearing a precise multivalent display of the ER ligand on a monodisperse water-soluble scaffold. Indeed, this approach may be used to generate a library of compounds bearing a precise multivalent display of ER ligands on a monodisperse water-soluble scaffold. See FIG. 13A (n=2 to 10), for schematic of such multivalent estradiol conjugates. FIG. 14B depicts the chemical structure of a hexavalent peptoid estradiol conjugate, the activity of which has been tested and quantitated as described below.

Materials and Methods

Mammalian Cell Extracts: MCF-7 cells were grown to ~80% confluence in 10-cm culture dishes and harvested in 5 ml ice cold phosphate buffered saline (PBS). Cell suspensions were centrifuged and the pellets were snap frozen on dry ice to lyse the cells. Cell pellets were resuspended in 500 μl freshly prepared receptor buffer (50 mM NaCl, 10 mM Tris pH 7.5, 1 mM EDTA, 1 mM DTT (dithiothreitol), 15 mM MgCl$_2$, 20 mM sodium molybdate, 20% glycerol, 1 μg/μl protease inhibitor), and incubated on ice for 10 min. The lysates were centrifuged for 20 min at 15,000×g for 20 min at 4° C. The protein concentration of each supernatant was assayed using a Bio-Rad protein assay and was typically between 1-2 μg/μl.

Competitive Binding Assays: Cell extracts were incubated with $1.0 \times 10^{-8}$ M radiolabeled ligand ($^3$H-Estradiol) in the presence or absence of increasing concentrations of unlabeled ligand in a final volume of 100 μl of receptor buffer. Following 18 hr incubation at 4° C., cell extracts were mixed with an equal volume of a 10 mg/ml activated charcoal suspended in receptor buffer and incubated on ice for 10 mM. The activated charcoal/cell extract slurry was centrifuged at 12,000×g for 3 minutes. 180 μl cell extract supernatant was added to 2 ml scintillation fluid and $^3$H decay was counted for 3 minutes on a scintillation counter. Binding was computed as scintillation counts per minute (cpm) in the absence of unlabeled ligand minus cpm in the presence of unlabeled ligand. Non-linear regression analyses were performed using Graph-Pad Prizm® software.

Luciferase Assays: Human Embryonic Kidney (HEK) 293T cells were plated onto 24 well plates coated with poly-D lysine and grown to ~70% confluence in yellow Dulbecco's Modified Eagles Media (DMEM) containing 5% charcoal-stripped fetal bovine serum (CS-FBS). Cells were stably transfected with xETL, pCMV(LacZ), Bluescript and either pcDNA3(wtER) or pcDNA3(Vo) plasmids. Cells were allowed to recover in yellow DMEM containing 5% CS-FBS for 6 hrs and then serum starved for 12 hrs in yellow DMEM containing 0% CS-FBS before ligand treatment. Cells were then treated with 100 nM final concentration of respective ligand in EtOH for 18 hrs before harvesting. After harvesting, the cells were incubated in Promega™ lysis buffer for 30 min at room temperature. Cell lysates were plated in duplicate on 96-well plates, reacted with luciferase assay buffer (Promega), and read on an Lmax plate reader. To test transfection efficiency and for normalization, cell lysates were plated in duplicate on 96-well plates, reacted with LacZ buffer, and read on a Molecular Biosystems plate reader to assay β-gal activity. Data were processed using the Microsoft Excel spreadsheet program.

Results

Figure 14:
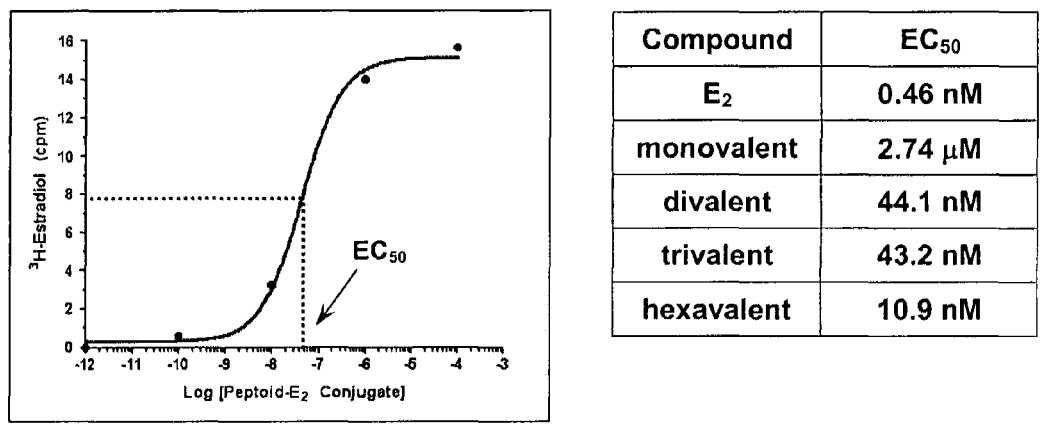
FIG. 14 shows a saturation curve of hormone binding in MCF-7 whole cell lysates. MCF-7 cell extracts were prepared from logarithmically growing MCF-7 cells and hormone binding activity was measured as described in Example VI. Peptoid Estradiol conjugates: monovalent, divalent, trivalent, and hexavalent; E2: 17β-estradiol. For clarity, the inset shows binding activity of the trivalent conjugate only.

In accordance with the present invention, monovalent, divalent, trivalent, and hexavalent peptoid estradiol conjugates were synthesized. MCF-7 cell extracts were prepared from logarithmically growing MCF-7 cells and binding of monovalent, divalent, trivalent, and hexavalent peptoid estradiol conjugates to purified ER was evaluated by competitive radiometric assay as described herein. As shown in FIG. 14, increasing the valency of estradiol presentation is correlated with an increase in avidity of binding between the peptoid estradiol conjugates and ER present in the cellular extracts. Binding avidity of the peptoid estradiol conjugates is compared to the positive control of 17β-estradiol (E2). The inset of FIG. 14 shows a saturation curve of binding activity for the trivalent peptoid estradiol conjugate.

Figure 15:
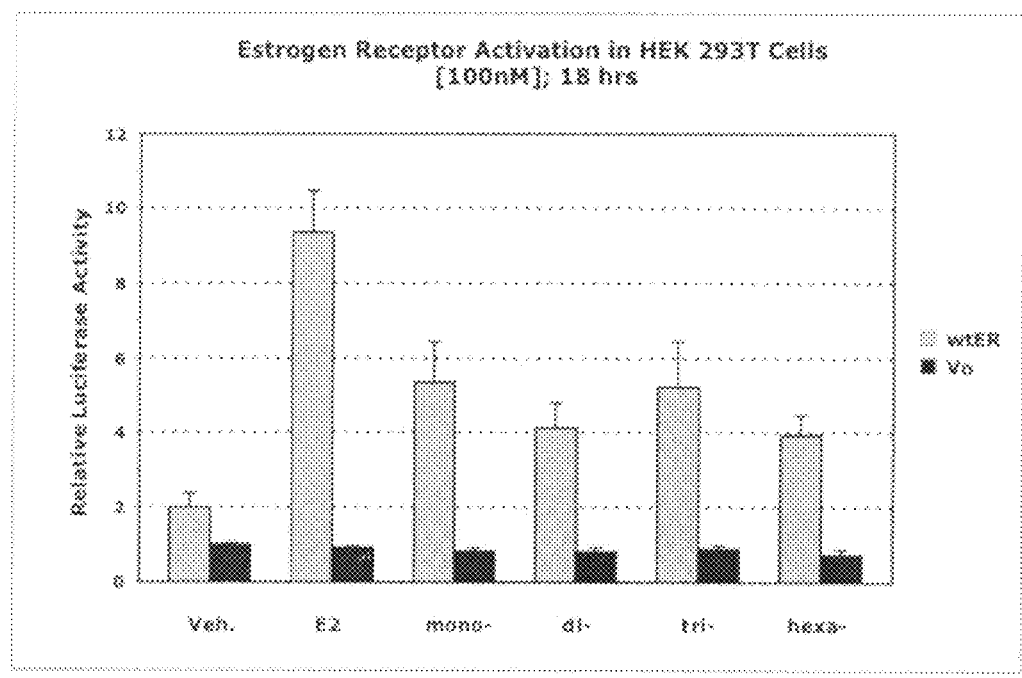
FIG. 15 shows a histogram of relative luciferase activity of lysates derived from estrogen receptor positive (wtER) and estrogen receptor negative (Vo) human embryonic kidney (HEK) 293T cells. ER+ (wtER) and ER− (Vo) HEK 293T cells were stably transfected with plasmids containing ER-responsive luciferase reporter genes. Cells were treated for 18 hrs with 100 nM concentrations of the indicated ligand. Peptoid Estradiol conjugates: mono- (monovalent), di- (divalent), tri- (trivalent), and hexa- (hexavalent); E2: 17β-estradiol; Vehicle: EtOH.

The peptoid estradiol conjugates were also assessed with respect to their ability to activate genomic pathways downstream of the estrogen receptor (ER). Briefly, ER+ (wtER) and ER− (Vo) human embryonic kidney (HEK) 293T cells were stably transfected with plasmids containing ER-responsive luciferase reporter genes. These transfected cell lines were used as cell based assays to measure transcriptional activation triggered by ER engagement. Cells were treated for 18 hrs with 100 nM concentrations of the indicated ligand. Luciferase reporter assays were used to assess activation. As shown in FIG. 15, all of the peptoid estradiol conjugates stimulated an increase in transcription of ER responsive luciferase reporter genes as measured by an increase in luciferase activity.

One of skill in the art would also appreciate that genomic mechanisms of ER action may also be evaluated using other protocols, such as those that call for reverse transcriptase polymerase chain reaction (RT-PCR) amplification of transcripts of genes known to be regulated on a transcriptional level by ER engagement.

Similar cell based systems may also be used to measure activation of non-genomic signaling pathways. For such applications, cell lysates would be prepared for subsequent Western Blot analysis of, for example, phosphorylated targets. Fluorescently labeled conjugates may also be used to visualize their sub-cellular localization.

As indicated above, the present method may be used to generate a library of compounds bearing a precise multivalent display of ER ligands on a monodisperse water-soluble scaffold. Moreover, new synthetic routes will also be established for the precise multivalent display of estradiol conjugates. Diverse sequences so generated will be screened to identify species that are excluded from trafficking to the nucleus and are thus capable of selectively activating membrane-associated ER signaling. The biological activity of such compounds will be rigorously evaluated in human breast cancer cell lines such as, for example, ER(+) MCF-7 and in ER(−) control cell lines. Large estradiol conjugates are anticipated to evoke a specific subset of ER-mediated pathways within the cell. Although not limiting with respect to the novel macromolecular estradiol conjugates of the present invention, it has been observed that increasing the size and charge of estrogen conjugates mitigates their capability to traffic to the nucleus (Patch et al., *Curr. Opin. Chem. Biol.*, 2002, 6, 872). In addition, the binding of macromolecular estradiol conjugates to the ER may sterically block the association of protein co-activators or occlude functional interactions with estrogen response elements on target gene promoters. As a result, genomic responses to ER signaling may be selectively abrogated. Correspondingly, these effects may facilitate more rigorous examination of nongenomic actions of estrogen.

Novel macromolecular estradiol conjugates of the present invention may be found that curtail the ability of ligand-activated ER to evoke genomic responses, thus yielding a family of lead compounds for improved hormone replacement therapy and for the inhibition of hormone-responsive breast cancer proliferation. The significance of such research will be the discovery of a new family of molecules to study and control the function of estrogen hormone receptors, which play a crucial role in the development of many breast cancers.

Figure 16:
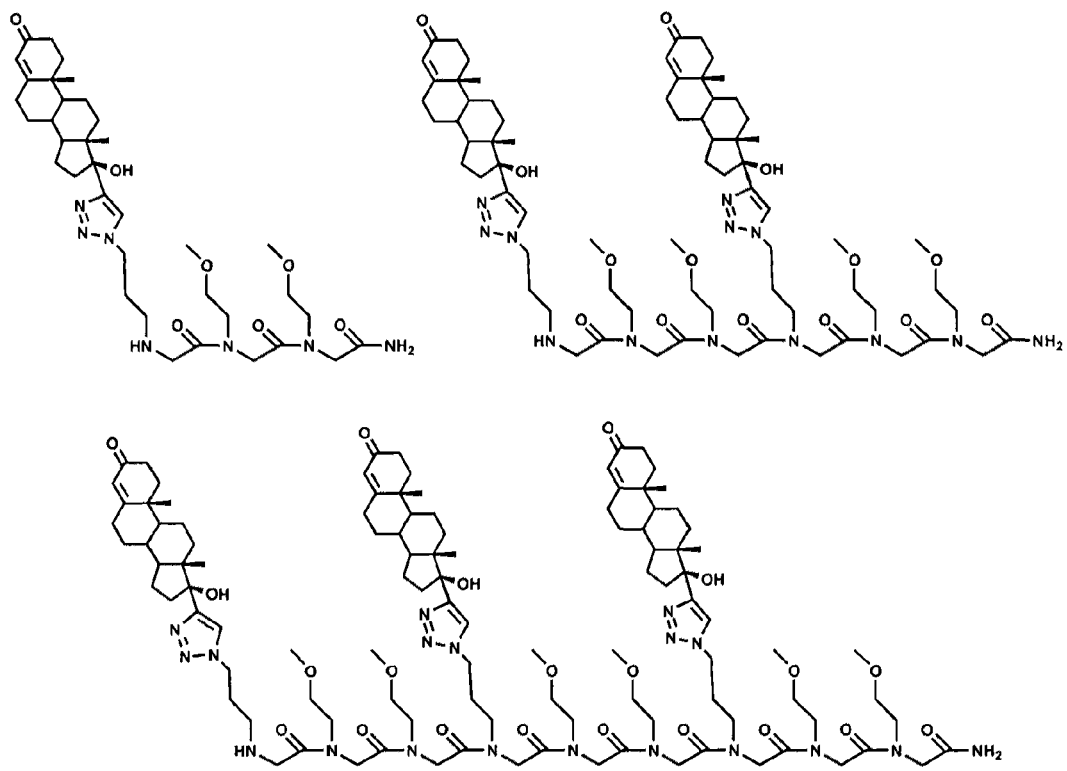
FIG. 16 depicts chemical structures of several peptoid ethisterone conjugates.

The present method may, for example, be used to generate peptoid-ethisterone conjugates such as those shown in FIG. 16. Compounds in FIG. 16 show mono-, di- and trivalent display of the progesterone receptor ligand ethisterone. Briefly, azide-containing peptoid scaffolds were synthesized on solid-phase support as described herein. Ethisterone was efficiently conjugated to the molecular scaffold using the CuCAAC reaction, resulting in a 1,2,3 triazole linkage between the receptor ligand and the peptoid scaffold. Compounds shown here may be used to study agonist or antagonist effects with a diverse array of sex steroid hormone receptors.

Similar approaches may be applied to the development of macromolecular conjugates designed to target prostate cancer cells and other hormone responsive tumors. In accordance with the present invention, multivalent androgen conjugates, for example, may be synthesized and tested in cell based assays, which are known to skilled practitioners, to evaluate their potential as diagnostic and/or therapeutic compounds. Other hormone responsive tumors include, without limitation, kidney and pituitary tumors.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A linear oligomer comprising a plurality of identical backbone-attached pendant groups, wherein each of the identical backbone-attached pendant groups is attached to the backbone via a triazole linkage group.

2. The linear oligomer of claim 1, wherein the oligomer comprises between 2-1,000 monomers.

3. The linear oligomer of claim 1, wherein the oligomer comprises between 2-100 monomers.

4. The linear oligomer of claim 1, wherein the oligomer comprises between 2-25 monomers.

5. The linear oligomer of claim 1, wherein the oligomer is mono-valent, di-valent, tri-valent, tetra-valent, penta-valent, hexa-valent, hepta-valent, octa-valent, nona-valent, and deca-valent.

6. The linear oligomer of claim 1, wherein the backbone-attached pendant groups comprise hormone receptor ligands, cell surface receptor ligands, tumor specific antigen ligands, cytotoxic agents, pharmaceutical moieties, fluorophores, chelates, radioisotopes, affinity tags, or antibiotic moieties.

7. The linear oligomer of claim 1, wherein the backbone-attached pendant group is attached to the backbone via a triazole linkage group, and the triazole linkage group is formed by transformation of ethynyl or azido of the pendant group.

8. The linear oligomer of claim 7, wherein the transformation of ethynyl or azido of the pendant group occurs via azide-alkyne [3+2]-cycloaddition conjugation.

9. A polyvalent linear oligomer of claim 1, wherein the backbone-attached pendant groups comprise steroid hormone receptor ligands.

10. The linear oligomer of claim 1, wherein the backbone-attached pendant groups comprise hormone receptor ligands, and the hormone receptor ligand is 17a-ethynyltestosterone, 17a-ethynylestrdiol, norgestimate, 17a-proynylestradiol, or 17a-butynylestradiol:

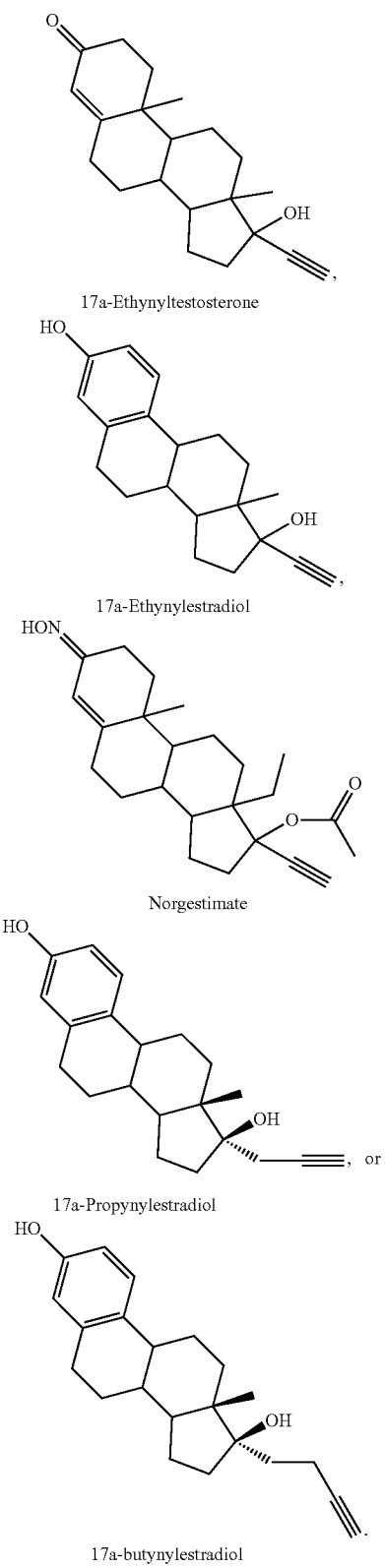

11. The linear oligomer of claim 1, wherein the backbone-attached pendant groups comprise hormone receptor ligands, and each hormone receptor ligand is attached to the backbone via a triazole linkage which is formed through the transformation of the triple bond of the hormone receptor ligand.

12. The linear oligomer of claim 1, wherein the backbone-attached pendant groups comprise hormone receptor ligands; each hormone receptor ligand is attached to the backbone via a triazole linkage which is formed via azide-alkyne [3+2]-cycloaddition conjugation.

13. The linear oligomer of claim 1, wherein the pendant groups are selected from phenyl propargyl ether, (4-pentylphenyl)ethyne, (4-fluoro-3-methylphenyl)ethyne, 3-phenylpropyne, and ethynylferrocene; and each pendant group is attached to the backbone via a triazole linkage which is formed through the transformation of the triple bond of the pendant group.

14. The linear oligomer of claim 1, wherein the pendant groups are selected from phenyl propargyl ether, (4-pentylphenyl)ethyne, (4-fluoro-3-methylphenyl)ethyne, 3-phenylpropyne, and ethynylferrocene; and each pendant group is attached to the backbone via a triazole linkage which is formed via azide-alkyne [3+2]-cycloaddition conjugation.

15. The linear oligomer of claim 1, wherein the pendant groups are selected from

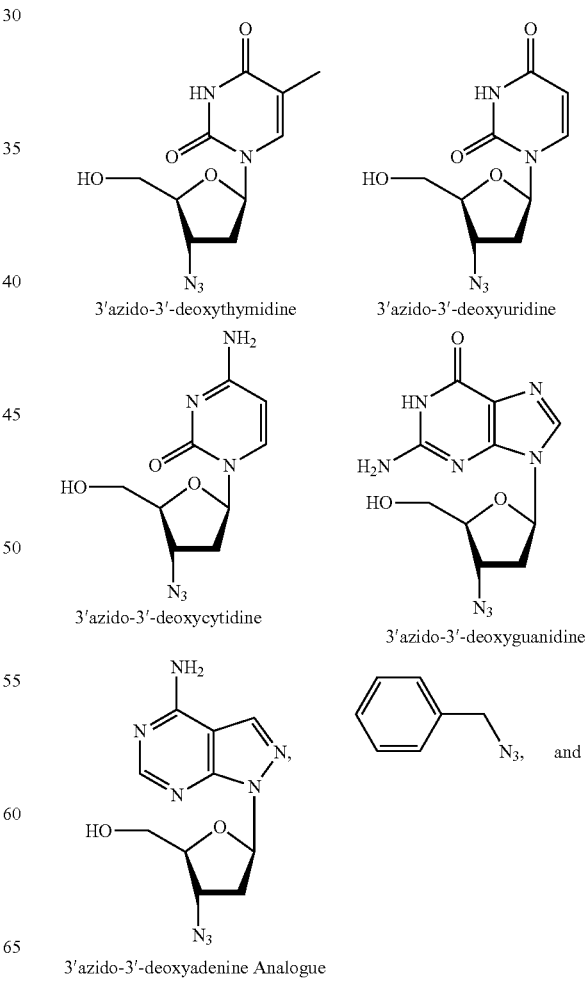

-continued

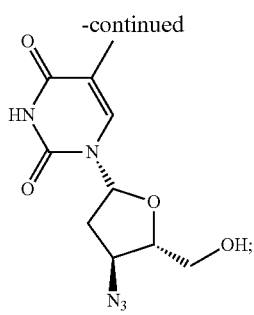

and each pendant group is attached to the backbone via a triazole linkage which is formed through the transformation of the azido group of the pendant group.

16. The linear oligomer of claim 1, wherein the backbone comprises N-substituted glycine monomers.

17. The linear oligomer of claim 1, wherein the backbone comprises N-substituted glycine monomers, and the substitution on the N is methoxyethyl, aminopropyl, aminobutyl, imidazoethyl, imidazomethyl, benzyl, phenethyl, naphthylmethyl, or guanidinopropyl.

18. The linear oligomer of claim 1, wherein the polyvalent linear oligomer is

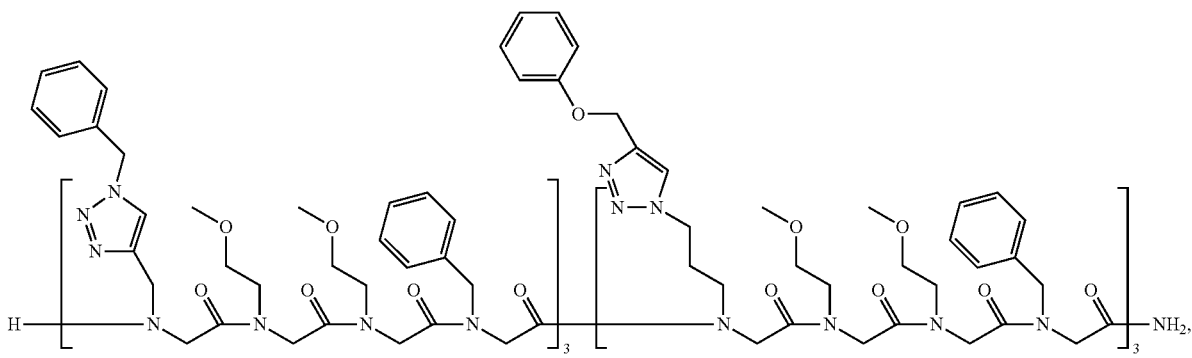

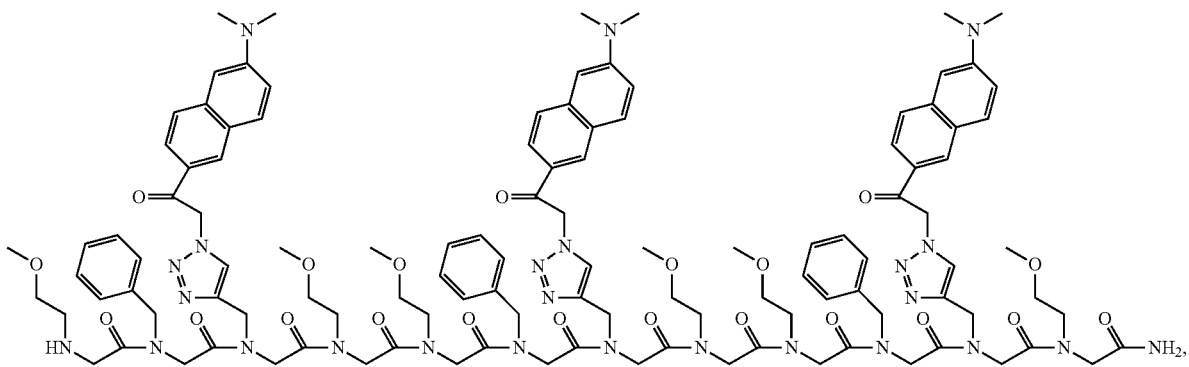

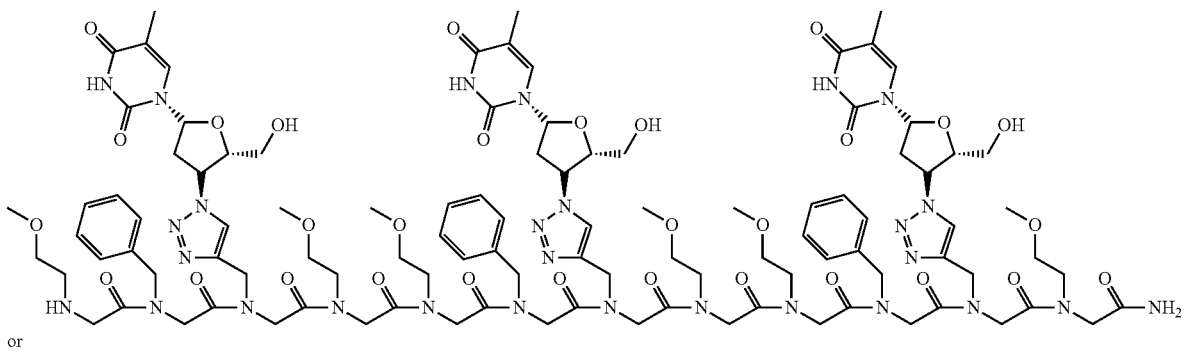

or

-continued
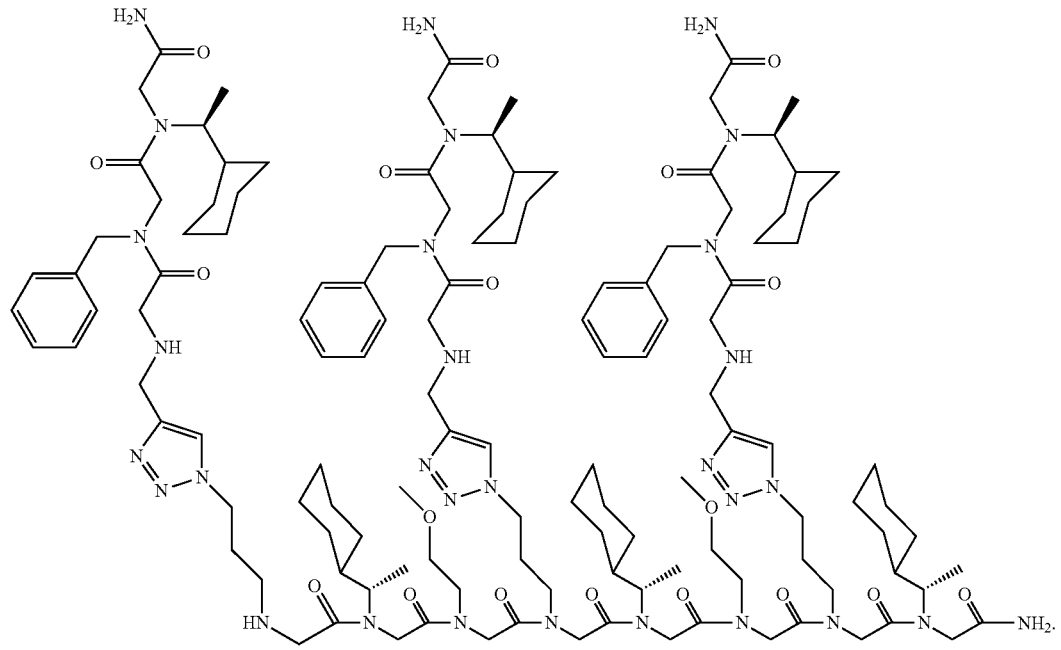 [SMILES: COCCN(CC(=O)N(CCCn1cc(CNCC(=O)N(CC(=O)N(CC(N)=O)[C@@H](C)C2CCCCC2)Cc2ccccc2)nn1)CC(=O)N(CC(=O)N(CCOC)CC(=O)N(CCCn1cc(CNCC(=O)N(CC(=O)N(CC(N)=O)[C@@H](C)C2CCCCC2)Cc2ccccc2)nn1)CC(=O)N(CC(N)=O)[C@@H](C)C1CCCCC1)[C@@H](C)C1CCCCC1)C(=O)CN(C(=O)CNCCCn1cc(CNCC(=O)N(CC(=O)N(CC(N)=O)[C@@H](C)C2CCCCC2)Cc2ccccc2)nn1)[C@@H](C)C1CCCCC1]
19. The linear oligomer of claim 1, wherein the polyvalent linear oligomer is
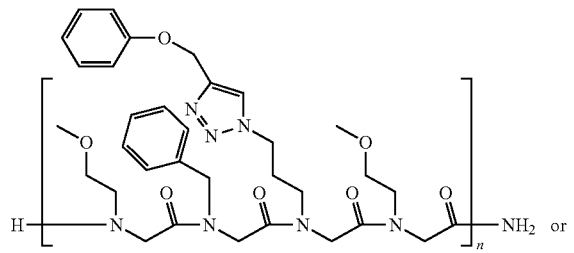
-continued
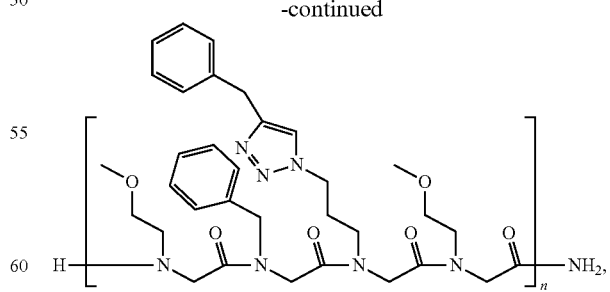
and wherein n is 3 or 6.
20. The linear oligomer of claim 1, wherein the polyvalent linear oligomer is

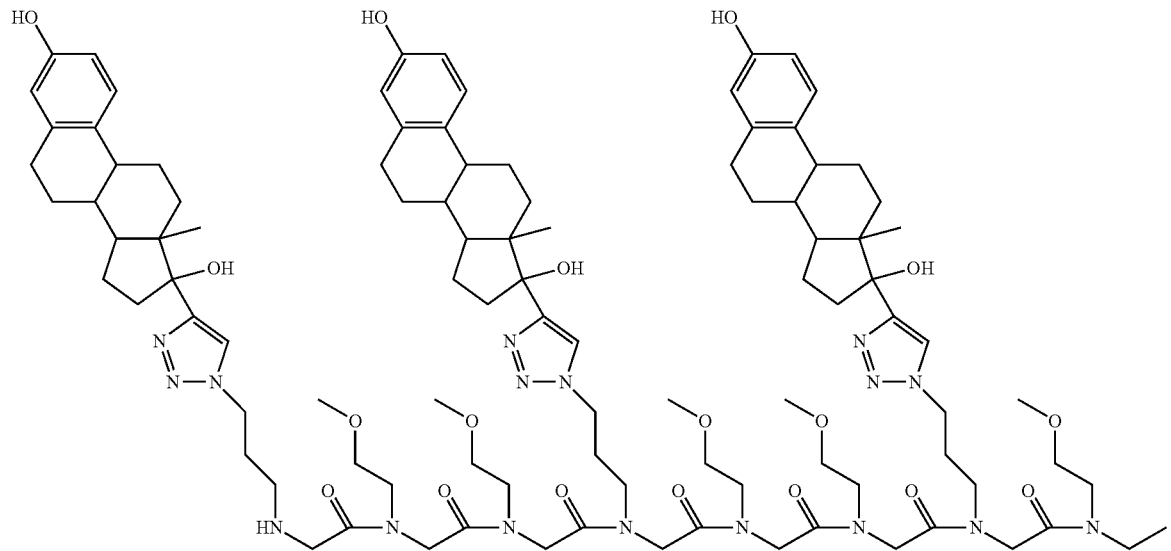
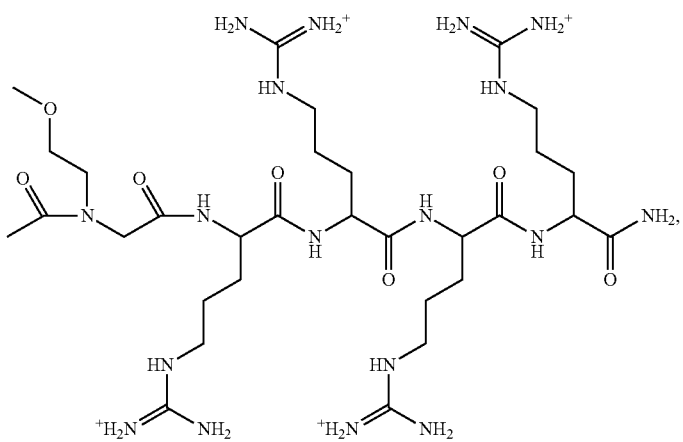
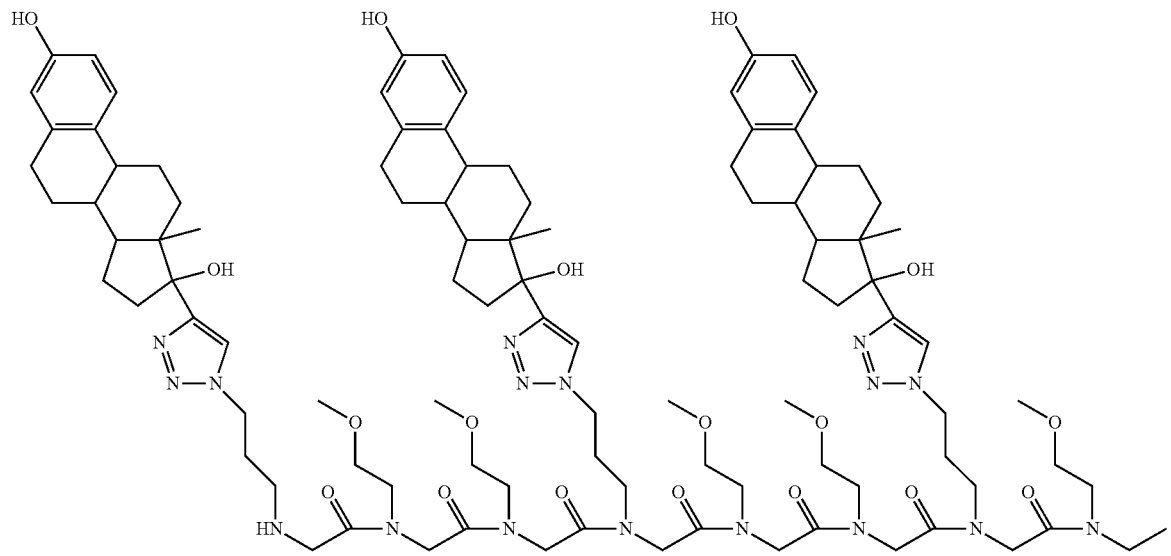

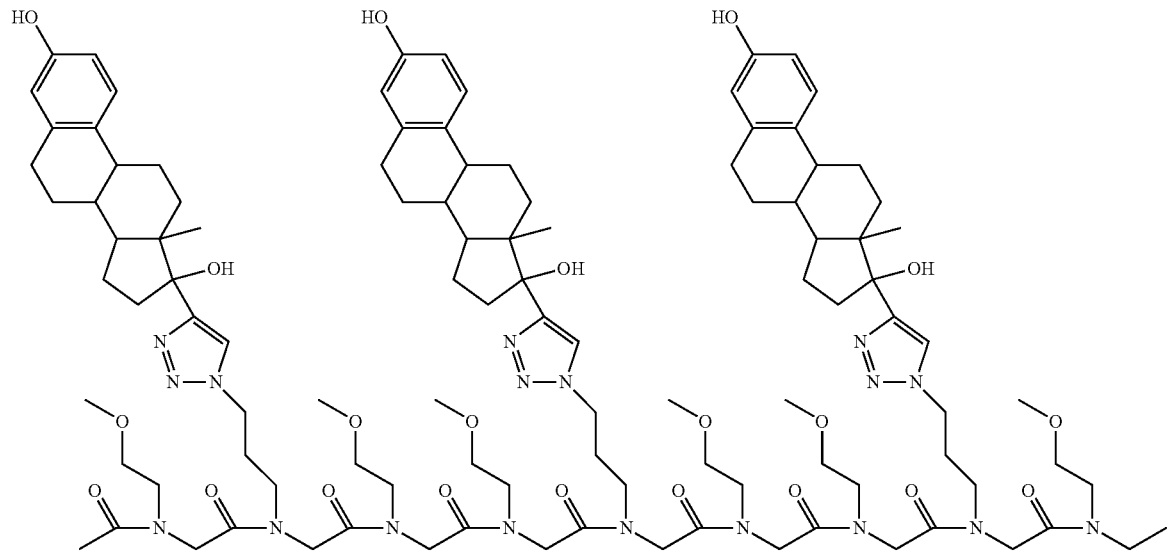
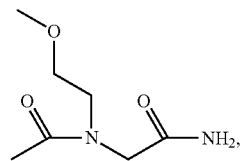
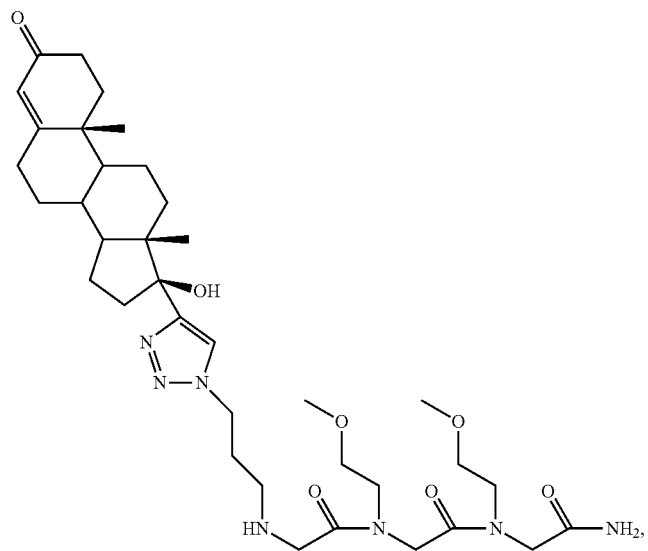

-continued
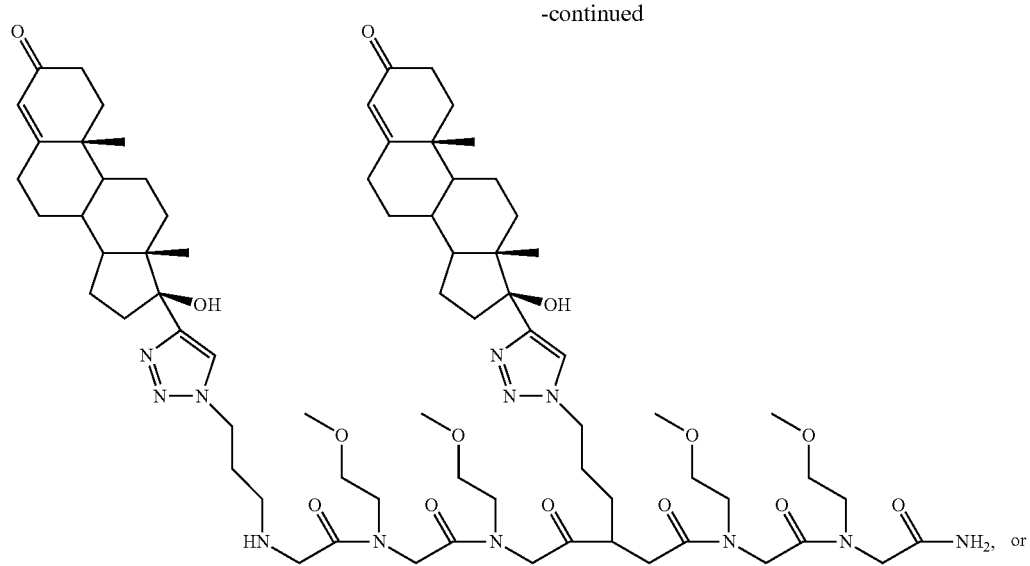
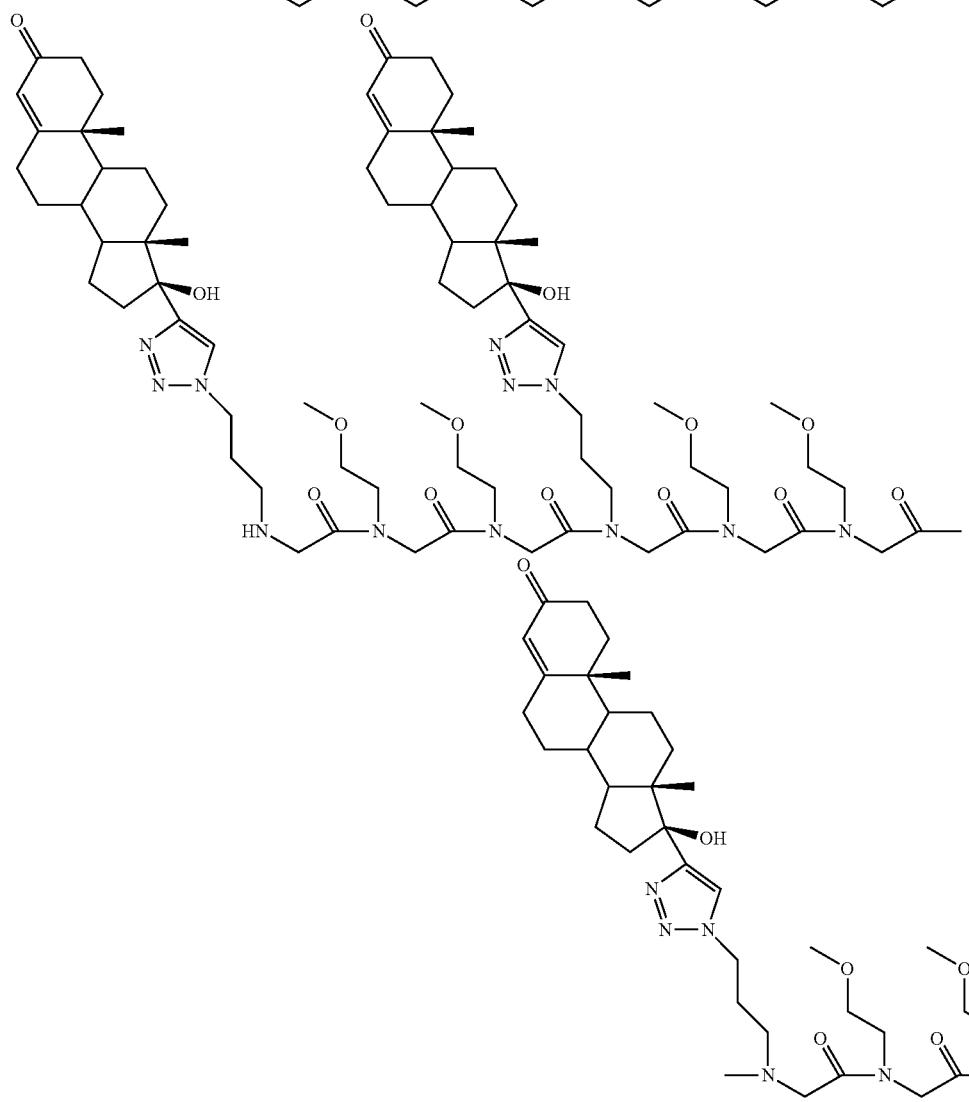
21. The linear oligomer of claim 1, wherein the polyvalent linear oligomer is

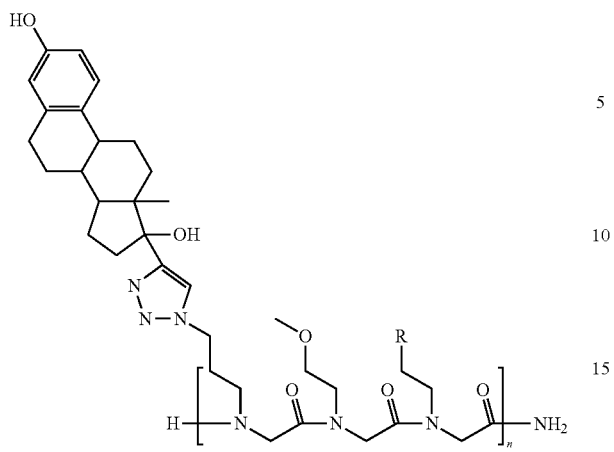
and wherein n is 2, 3, 4, 5, 6, 7, 8, 9, or 10; and
R is 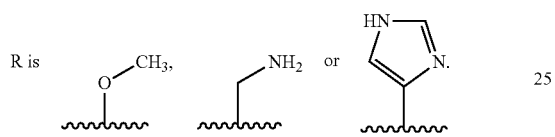
* * * * *